(12) United States Patent
Shin et al.

(10) Patent No.: US 7,732,598 B2
(45) Date of Patent: Jun. 8, 2010

(54) TRIAZINE-BASED COMPOUND, METHOD OF MAKING THE SAME, AND AN ORGANIC LIGHT-EMITTING DEVICE INCLUDING THE SAME

(75) Inventors: Jung-Han Shin, Suwon-si (KR);
Seok-Jong Lee, Suwon-si (KR);
Chang-ho Lee, Suwon-si (KR); Seok Hwan Hwang, Suwon-si (KR);
Seung-Gak Yang, Suwon-si (KR);
Young-Kook Kim, Suwon-si (KR);
Hee-Yeon Kim, Suwon-si (KR)

(73) Assignee: Samsung Mobile Display Co., Ltd., Suwon-si, Gyeonggi-do (KR)

( * ) Notice: Subject to any disclaimer, the term of this patent is extended or adjusted under 35 U.S.C. 154(b) by 995 days.

(21) Appl. No.: 11/487,440

(22) Filed: Jul. 17, 2006

(65) Prior Publication Data

US 2007/0015007 A1 Jan. 18, 2007

(30) Foreign Application Priority Data

Jul. 15, 2005 (KR) ...................... 10-2005-0064059

(51) Int. Cl.
*C07D 251/24* (2006.01)

(52) U.S. Cl. ...................... 544/180; 313/504; 313/506; 428/690

(58) Field of Classification Search ................. 544/180
See application file for complete search history.

(56) References Cited

U.S. PATENT DOCUMENTS

| 6,225,467 | B1 * | 5/2001 | Esteghamatian et al. ..... 544/180 |
| 6,352,791 | B1 | 3/2002 | Fink et al. |
| 6,559,256 | B2 | 5/2003 | Holmes et al. |
| 6,821,643 | B1 * | 11/2004 | Hu et al. ..................... 428/690 |
| 2004/0191191 | A1 * | 9/2004 | Ehlis et al. .................... 424/59 |

FOREIGN PATENT DOCUMENTS

KR 10-2000-0064244 11/2000

\* cited by examiner

*Primary Examiner*—David Wu
*Assistant Examiner*—Vu Nguyen
(74) *Attorney, Agent, or Firm*—Lee & Morse, P.C.

(57) ABSTRACT

A triazine-based compound having three biphenyl groups, represented by Structure 1, below, wherein $R_1$ through $R_{18}$ are each independently one of: hydrogen, a substituted $C_{1-30}$ alkyl group, an unsubstituted $C_{1-30}$ alkyl group, a substituted $C_{6-50}$ aryl group, an unsubstituted $C_{6-50}$ aryl group, a substituted $C_{4-50}$ heteroaryl group, and an unsubstituted $C_{4-50}$ heteroaryl group, and at least one of $R_1$, $R_2$, $R_7$, $R_8$, $R_{13}$ and $R_{14}$ is one of: a substituted $C_{1-30}$ alkyl group, an unsubstituted $C_{1-30}$ alkyl group, a substituted $C_{6-50}$ aryl group, an unsubstituted $C_{6-50}$ aryl group, a substituted $C_{4-50}$ heteroaryl group, and an unsubstituted $C_{4-50}$ heteroaryl group.
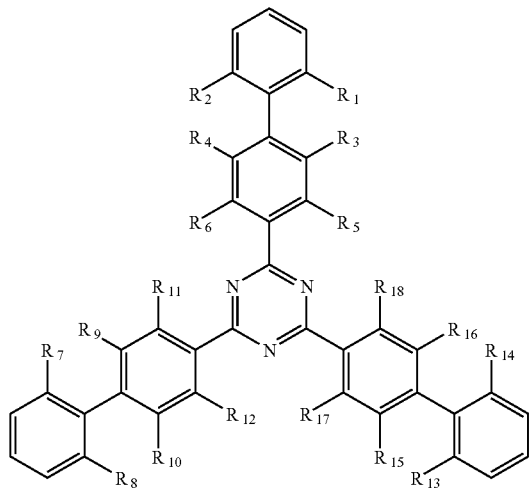
(1)
20 Claims, 12 Drawing Sheets

TRIAZINE-BASED COMPOUND, METHOD OF MAKING THE SAME, AND AN ORGANIC LIGHT-EMITTING DEVICE INCLUDING THE SAME

BACKGROUND OF THE INVENTION

1. Field of the Invention

The present invention relates to a triazine-based compound and an organic light-emitting device employing the same. More particularly, the present invention relates to a triazine-based compound which may exhibit electric stability, high electron transport capability, high hole-blocking capability, high glass transition temperature and/or resistance to crystallization, a method of making the same and an organic light-emitting device including the same.

2. Description of the Related Art

Electroluminescent emitting devices are self-emitting devices that may have wide viewing angles, excellent contrast and quick response times and, accordingly, have attracted much attention. Electroluminescent emitting devices can be classified into inorganic light-emitting devices, which include emitting layers of inorganic compounds, and organic light-emitting devices (OLEDs), which include emitting layers of organic compounds. Organic light-emitting devices may be brighter and may have a lower operating voltage and a quicker response time compared to inorganic light-emitting devices. Furthermore, organic light-emitting devices may realize multicolor images. Due to these and other advantages of organic light-emitting devices, extensive research into organic light-emitting devices is ongoing.

Typically, an organic light-emitting device has an anode/organic emissive layer/cathode structure. An organic light-emitting device may include a hole-blocking layer or an electron injection layer between the organic emissive layer and the cathode. Thus, the organic light-emitting device may have an anode/organic emissive layer/hole-blocking layer/cathode structure, an anode/organic emissive layer/electron transport layer/cathode structure, and/or an anode/organic emissive layer/hole-blocking layer/electron injection layer/cathode structure, etc.

The electron transport layer may be formed of, e.g., a heteroaromatic compound such as an oxadiazol, a thiadiazol or a pyrimidine. However, when conventional materials are used to form the electron transport layer or the hole-blocking layer of an organic light-emitting device, the lifespan, efficiency and driving voltage of the organic light-emitting device may not be satisfactory. Accordingly, there is a need for compounds in which these properties are enhanced.

SUMMARY OF THE INVENTION

The present invention is therefore directed to a triazine-based compound, a method of making the same and an organic light-emitting device including the same, which substantially overcome one or more of the problems due to the limitations and disadvantages of the related art.

It is therefore a feature of an embodiment of the present invention to provide a triazine-based compound suitable for use in an organic light-emitting device that exhibits enhanced lifespan and efficiency and reduced power consumption.

It is therefore another feature of an embodiment of the present invention to provide an organic light-emitting device including a triazine-based compound that exhibits enhanced lifespan and efficiency and reduced power consumption.

At least one of the above and other features and advantages of the present invention may be realized by providing a triazine-based compound having three biphenyl groups, represented by Structure 1, below,

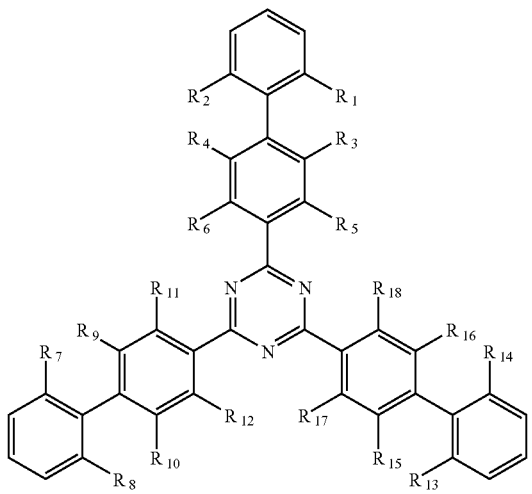

(1)

wherein $R_1$ through $R_{18}$ may each be independently one of hydrogen, a substituted $C_{1-30}$ alkyl group, an unsubstituted $C_{1-30}$ alkyl group, a substituted $C_{6-50}$ aryl group, an unsubstituted $C_{6-50}$ aryl group, a substituted $C_{4-50}$ heteroaryl group, and an unsubstituted $C_{4-50}$ heteroaryl group, and at least one of $R_1$, $R_2$, $R_7$, $R_8$, $R_{13}$ and $R_{14}$ may be one of a substituted $C_{1-30}$ alkyl group, an unsubstituted $C_{1-30}$ alkyl group, a substituted $C_{6-50}$ aryl group, an unsubstituted $C_{6-50}$ aryl group, a substituted $C_{4-50}$ heteroaryl group, and an unsubstituted $C_{4-50}$ heteroaryl group.

Substituents of the alkyl group, the aryl group and the heteroaryl group may include at least one of —F; —Cl; —Br; —CN; —NO$_2$; —OH; a $C_{1-10}$ alkyl group that is unsubstituted; a $C_{1-10}$ alkyl group that is substituted with at least one of —F, —Cl, —Br, —CN, —NO$_2$ and —OH; a $C_{1-10}$ alkoxy group that is unsubstituted; a $C_{1-10}$ alkoxy group that is substituted with at least one of —F, —Cl, —Br, —CN, —NO$_2$ and —OH; a $C_{6-10}$ aryl group that is unsubstituted; a $C_{6-10}$ aryl group that is substituted with at least one of —F, —Cl, —Br, —CN, —NO$_2$ and —OH; a $C_{4-10}$ heteroaryl group that is unsubstituted; and a $C_{4-10}$ heteroaryl group that is substituted with at least one of —F, —Cl, —Br, —CN, —NO$_2$ and —OH.

$R_1$, $R_7$ and $R_{13}$ may be identical, $R_2$, $R_8$ and $R_{14}$ may be identical, $R_3$, $R_9$ and $R_{15}$ may be identical, $R_4$, $R_{10}$ and $R_{16}$ may be identical, $R_5$, $R_{11}$ and $R_{17}$ may be identical, and $R_6$, $R_{12}$ and $R_{18}$ may be identical.

One of $R_1$ and $R_2$ may be a methyl group and the other may be hydrogen, one of $R_7$ and $R_8$ may be a methyl group and the other may be hydrogen, and one of $R_{13}$ and $R_{14}$ may be a methyl group and the other may be hydrogen. $R_3$, $R_4$, $R_5$, $R_6$, $R_9$, $R_{10}$, $R_{11}$, $R_{12}$, $R_{15}$, $R_{16}$, $R_{17}$, and $R_{18}$ may each be hydrogen.

One of $R_1$ and $R_2$ may be a phenyl group and the other may be hydrogen, one of $R_7$ and $R_8$ may be a phenyl group and the other may be hydrogen, and one of $R_{13}$ and $R_{14}$ may be a phenyl group and the other may be hydrogen. $R_3$, $R_4$, $R_5$, $R_6$, $R_9$, $R_{10}$, $R_{11}$, $R_{12}$, $R_{15}$, $R_{16}$, $R_{17}$, and $R_{18}$ may each be hydrogen.

The substitutions of $R_1$ through $R_{18}$ may be represented by one of structures 4 and 5, below, (4)

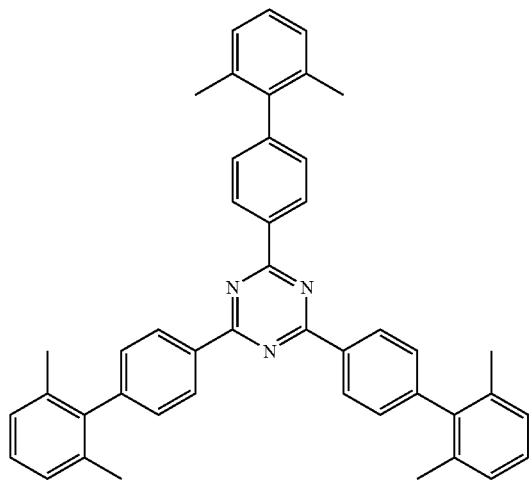

(5)

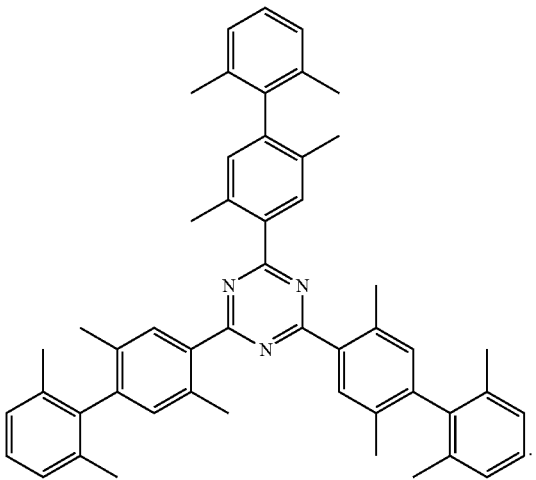

At least one of the above and other features and advantages of the present invention may also be realized by providing a method of making a triazine-based compound having three biphenyl groups including reacting a triazine ring-containing compound with a first biphenyl compound such that the biphenyl compound is bonded to a carbon of the triazine ring, wherein the first biphenyl compound includes moieties $R_a$ and $R_b$,

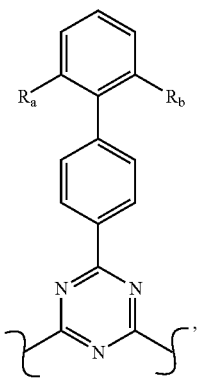

$R_a$ and $R_b$ are each independently one of hydrogen, a substituted $C_{1-30}$ alkyl group, an unsubstituted $C_{1-30}$ alkyl group, a substituted $C_{6-50}$ aryl group, an unsubstituted $C_{6-50}$ aryl group, a substituted $C_{4-50}$ heteroaryl group, and an unsubstituted $C_{4-50}$ heteroaryl group, and at least one of $R_a$ and $R_b$ is a substituted $C_{1-30}$ alkyl group, an unsubstituted $C_{1-30}$ alkyl group, a substituted $C_{6-50}$ aryl group, an unsubstituted $C_{6-50}$ aryl group, a substituted $C_{4-50}$ heteroaryl group, and an unsubstituted $C_{4-50}$ heteroaryl group.

Reacting the triazine ring-containing compound with the first biphenyl compound may result in three identical biphenyl groups bonded to carbons of the triazine ring. The first biphenyl compound may be prepared by reacting a first benzene ring-containing compound with a second benzene ring-containing compound, and the first benzene ring-containing compound may include a reactive moiety attached to a first carbon of the benzene ring, and a second moiety attached to the benzene ring ortho to the reactive moiety, wherein the second moiety corresponds to one of $R_a$ and $R_b$ and is not hydrogen. The triazine ring-containing compound may be a trihalotriazine.

At least one of the above and other features and advantages of the present invention may further be realized by providing an organic light-emitting device including a first electrode, a second electrode, and at least one organic layer interposed between the first and second electrodes, wherein the at least one organic layer includes a triazine-based compound having three biphenyl groups, represented by structure 1, below, (1)

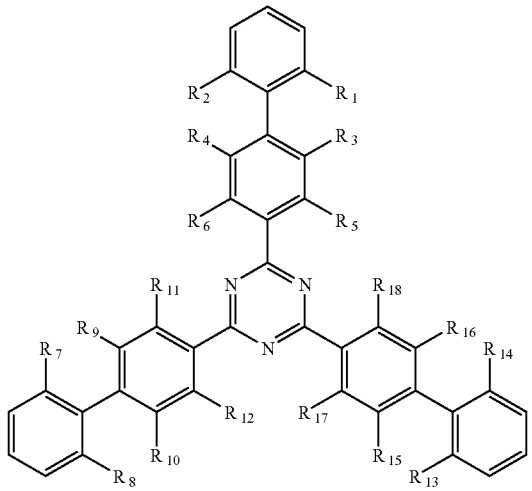

wherein $R_1$ through $R_{18}$ are each independently one of hydrogen, a substituted $C_{1-30}$ alkyl group, an unsubstituted $C_{1-30}$ alkyl group, a substituted $C_{6-50}$ aryl group, an unsubstituted $C_{6-50}$ aryl group, a substituted $C_{4-50}$ heteroaryl group, and an unsubstituted $C_{4-50}$ heteroaryl group, and at least one of $R_1$, $R_2$, $R_7$, $R_8$, $R_{13}$ and $R_{14}$ is one of a substituted $C_{1-30}$ alkyl group, an unsubstituted $C_{1-30}$ alkyl group, a substituted $C_{6-50}$ aryl group, an unsubstituted $C_{6-50}$ aryl group, a substituted $C_{4-50}$ heteroaryl group, and an unsubstituted $C_{4-50}$ heteroaryl group.

The at least one organic layer may form one of an emissive layer, a hole-blocking layer and an electron transport layer. The at least one organic layer may form an emissive layer, and the emissive layer may include a colored dopant. The colored dopant may be one of a red phosphorescent dopant, a green phosphorescent dopant, a blue phosphorescent dopant, a white phosphorescent dopant, a red fluorescent dopant, a green fluorescent dopant, a blue fluorescent dopant, and a white fluorescent dopant.

The at least one organic layer may form an emissive layer, and the device may further include a second organic layer that forms at least one of a hole-blocking layer and an electron transport layer, the second organic layer including the triazine-based compound having three biphenyl groups. The organic light-emitting device structure may be one of a first electrode/hole transport layer/emissive layer/electron transport layer/second electrode structure, a first electrode/hole injection layer/hole transport layer/emissive layer/electron transport layer/electron injection layer/second electrode structure, and a first electrode/hole injection layer/hole transport layer/emissive layer/hole-blocking layer/electron transport layer/electron injection layer/second electrode structure.

At least one of the above and other features and advantages of the present invention may still further be realized by providing a triazine-based compound having three biphenyl groups, represented by structure 1 below

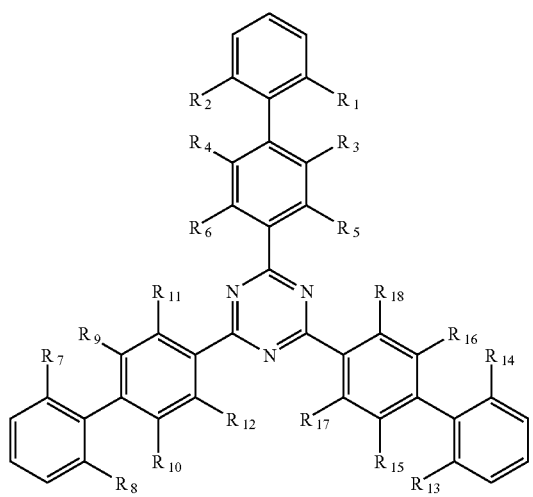

(1)

wherein $R_3$, $R_4$, $R_5$, $R_6$, $R_9$, $R_{10}$, $R_{11}$, $R_{12}$, $R_{15}$, $R_{16}$, $R_{17}$, and $R_{18}$ are, independently, one of hydrogen, an alkyl moiety of about 30 carbons or less, an aryl moiety of about 30 carbons or less, and a heteroaryl moiety of about 50 carbons or less, and at least one of $R_1$, $R_2$, $R_7$, $R_8$, $R_{13}$ and $R_{14}$ is a moiety effective to rotate the $C_1$-$C_1'$ bond of the biphenyl group to which it is attached, so as to disturb the conjugation between the rings of the biphenyl group.

The alkyl moiety of about 30 carbons or less may be one of a substituted $C_{1-30}$ alkyl group and an unsubstituted $C_{1-30}$ alkyl group, the aryl moiety of about 30 carbons or less may be one of a substituted $C_{6-50}$ aryl group and an unsubstituted $C_{6-50}$ aryl group, and the heteroaryl moiety of about 50 carbons or less may be one of a substituted $C_{4-50}$ heteroaryl group and an unsubstituted $C_{4-50}$ heteroaryl group.

BRIEF DESCRIPTION OF THE DRAWINGS

The above and other features and advantages of the present invention will become more apparent to those of ordinary skill in the art by describing in detail exemplary embodiments thereof with reference to the attached drawings in which.

DETAILED DESCRIPTION OF THE INVENTION

Figure 1A:
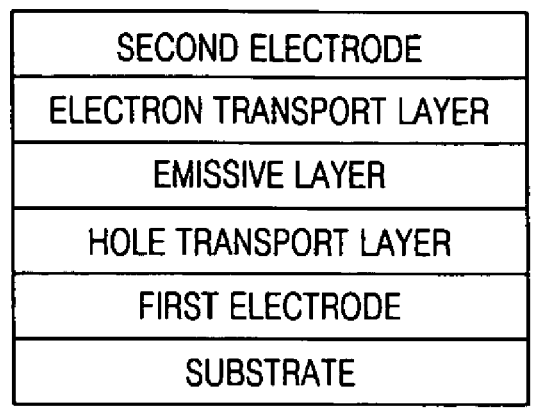
FIGS. 1A through 1C illustrate schematic sectional views of organic light-emitting devices according to embodiments of the present invention.

Korean Patent Application No. 10-2005-0064059, filed on Jul. 15, 2005, in the Korean Intellectual Property Office, and entitled: "Triazine-Based Compound and an Organic Light-Emitting Device Employing the Same," is incorporated by reference herein in its entirety.

The present invention will now be described more fully hereinafter with reference to the accompanying drawings, in which exemplary embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. In the figures, the dimensions of layers and regions are exaggerated for clarity of illustration. It will also be understood that when a layer is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

A triazine-based compound according to an embodiment of the present invention, Compound 1, is represented by Structure 1, below:

In the triazine-based compound, $R_1$ through $R_{18}$ may each be hydrogen, a substituted or unsubstituted $C_{1-30}$ alkyl group, a substituted or unsubstituted $C_{6-50}$ aryl group, or a substituted or unsubstituted $C_{4-50}$ heteroaryl group, provided that all of $R_1$, $R_2$, $R_7$, $R_8$, $R_{13}$ and $R_{14}$ are not hydrogen.

That is, in the three biphenyl groups bonded with the triazine ring, at least one of the six ortho positions $R_1$, $R_2$, $R_7$, $R_8$, $R_{13}$ and $R_{14}$ in the three aryl groups that are not directly connected to the triazine ring should be substituted, i.e., is not hydrogen. Of the six ortho positions, three or more may be substituted. In an implementation, all six ortho positions may be substituted.

When substituted as described above, the aryl groups in one or more of the biphenyl groups are not located in the same plane. That is, for a given biphenyl group, the structure of the biphenyl group may be distorted due to steric hindrance between the two aryl groups. Thus, conjugation between two aryl groups may be disrupted to enhance an energy gap of the compound.

For example, referring to the biphenyl group illustrated by Structure 1.10, below, steric hindrance between the aryl group that includes $C_1'$ and the aryl group that includes $C_1$ may cause the two aryl groups to be rotated with respect to each other along the $C_1'$-$C_1$ bond, thereby disturbing the conjugation between the two aryl groups.

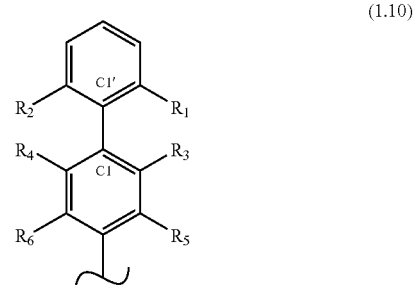

(1.10)

Compound 1 may be used to form an organic layer between an anode and a cathode of an organic light-emitting device. In particular, the compound may be used for a material that is used to form an emissive layer, an electron transport layer and a hole-blocking layer between the anode and the cathode of the organic light-emitting device.

The substituents of the alkyl group, the aryl group and the heteroaryl group may include at least one of —F; —Cl; —Br; —CN; —NO$_2$; —OH; a $C_{1-10}$ alkyl group that is unsubstituted or substituted with —F, —Cl, —Br, —CN, —NO$_2$ or —OH; a $C_{1-10}$ alkoxy group that is unsubstituted or substituted with —F, —Cl, —Br, —CN, —NO$_2$ or —OH; a $C_{6-10}$ aryl group that is unsubstituted or substituted with —F, —Cl, —Br, —CN, —NO$_2$ or —OH; and a $C_{4-10}$ heteroaryl group that is unsubstituted or substituted with —F, —Cl, —Br, —CN, —NO$_2$ or —OH.

More particularly, $R_1$ through $R_{18}$ may each be independently one of hydrogen, a methyl group, an ethyl group, a propyl group, a butyl group, a pentyl group, a hexyl group, a fluoromethyl group, a difluoromethyl group, a trifluoromethyl group, a phenyl group, a $C_{1-10}$ alkylphenyl group, a $C_{1-10}$ alkoxyphenyl group, a halophenyl group, a cyanophenyl group, a dicyanophenyl group, a trifluoromethoxyphenyl group, a o-, m-, or p-toly group, a o-, m- or p-cumenyl group, a mesityl group, a phenoxyphenyl group, a (α,α-dimethylbenzen)phenyl group, a (N,N'-dimethyl)aminophenyl group, a (N,N'-diphenyl)aminophenyl group, a pentalenyl group, an indenyl group, a naphthyl group, a $C_{1-10}$ alkylnaphthyl group, a $C_{1-10}$ alkoxynaphthyl group, a halonaphthyl group, a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrysenyl group, an ethylchrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coroneryl group, a trinaphthylenyl group, a heptaphenyl group, a heptacenyl group, a pyranthrenyl group, an ovalenyl group, a carbazolyl group, a $C_{1-10}$ alkyl carbazolyl group, a biphenyl group, a $C_{1-10}$ alkyl biphenyl group, $C_{1-10}$ alkoxy biphenyl group, a thiophenyl group, an indolyl group, a pyridyl group, a pyrazolyl group, an imidazolyl group, an oxazolyl group, a thiazolyl group, a triazolyl group, a tetrazolyl group, an oxadiazolyl group, a pyridinyl group, a pyridazinyl group, and a pyrimidinyl group, provided that all of $R_1$, $R_2$, $R_7$, $R_8$, $R_{13}$ and $R_{14}$ are not hydrogen.

In Compound 1, $R_1$, $R_7$ and $R_{13}$ may be identical, $R_2$, $R_8$ and $R_{14}$ may be identical, $R_3$, $R_9$ and $R_{15}$ may be identical, $R_4$, $R_{10}$ and $R_{16}$ may be identical, $R_5$, $R_{11}$, and $R_{17}$ may be identical, and $R_6$, $R_{12}$ and $R_{18}$ may be identical. That is, each of the three biphenyl groups may be the same.

Implementations of the triazine-based compound according to the present invention may include the compounds represented by Structures 2, 3, 4 and 5, below, but the present invention is not limited to these structures.

(2)

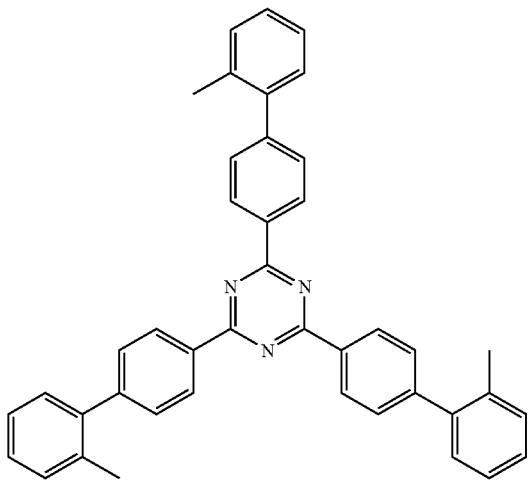

(3)

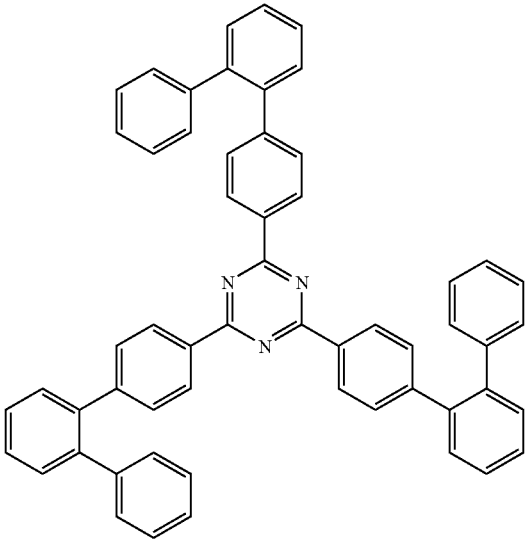

(4)

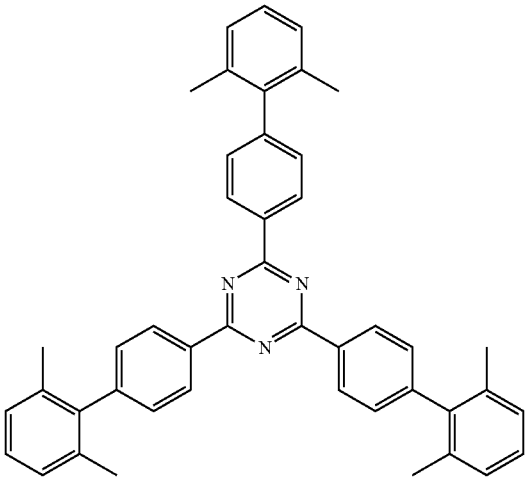

(5)

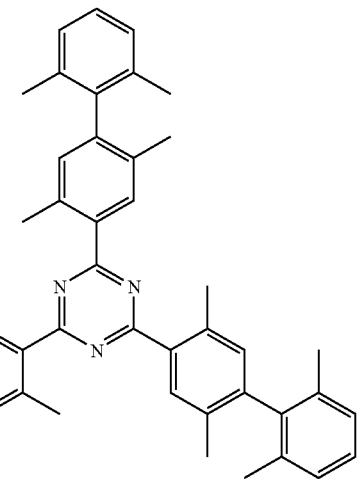

Compound 1 may be synthesized using organic synthesis. In an embodiment of the present invention, a method of manufacturing Compound 1 may include reacting a triazine ring-containing compound with one or more of a compound represented by Structure 1A, a compound represented by Structure 1B and a compound represented by Structure 1C.

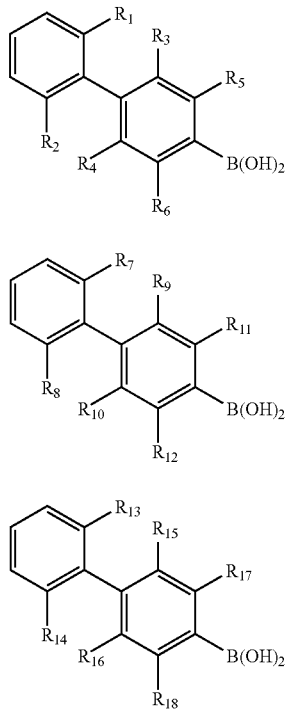

(1A)

(1B)

(1C)

Each of the biphenyl groups attached to the triazine ring may be different or may be the same, in which case $R_1$, $R_7$ and $R_{13}$ may be the same, $R_2$, $R_8$ and $R_{14}$ may be the same, $R_3$, $R_9$ and $R_{15}$ may be the same, $R_4$, $R_{10}$ and $R_{16}$ may be the same, $R_5$, $R_{11}$ and $R_{17}$ may be the same, and $R_6$, $R_{12}$ and $R_{18}$ may be the same.

Reaction Scheme 1, below, illustrates a method of synthesizing a compound according to the present invention, where the compound is represented by Structure 1':

Reaction Scheme 1

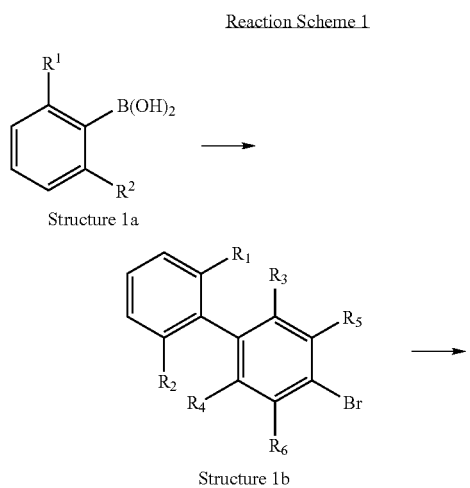

Structure 1a

Structure 1b

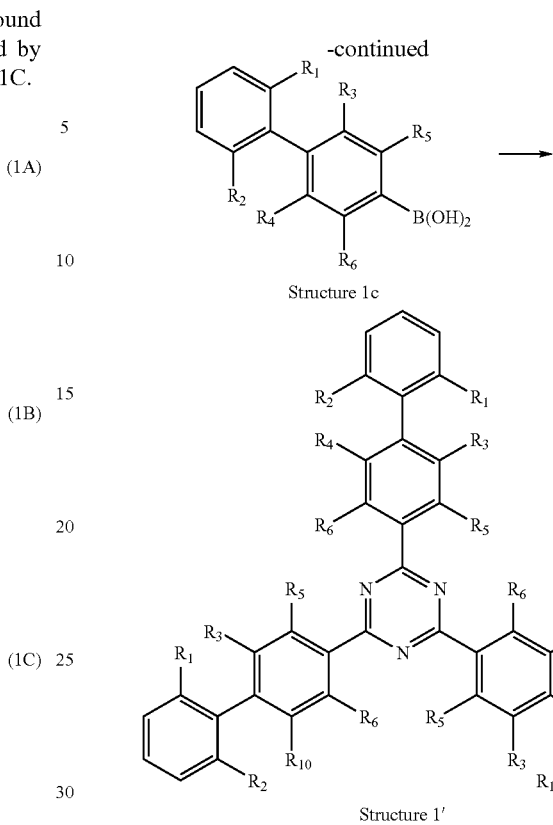

Structure 1c

Structure 1'

In Reaction Scheme 1, a compound may first be reacted with a bromophenyl-based compound, represented by Structure 1a, to produce the bromobiphenyl-based compound represented by Structure 1b. In Structure 1a, $R_1$ and $R_2$ may be as described above. In particular, one of $R_1$ and $R_2$ may be unsubstituted while the other may be substituted with the substituents described above. In Structure 1b, $R_3$, $R_4$, $R_5$ and $R_6$ may be unsubstituted or substituted with substituents described above.

The compound represented by Structure 1b may be reacted with butyl lithium and trimethoxy borate to produce the compound represented by Structure 1c. The temperature for the reactions may be, e.g., about −78° C., or from about −78° C. to about 0° C.

The triazine-based compound represented by Structure 1' may be obtained by reacting the compound represented by Structure 1c with a triazine ring-containing compound. The triazine ring-containing compound may be a trihalotriazine, e.g., trichlorotriazine.

Triazine-based compounds according to embodiments of the present invention may be used to fabricate organic light-emitting devices. An organic light-emitting device according to an embodiment of the present invention may include a first electrode, a second electrode and at least one organic layer that includes a triazine-based compound, e.g., Compound 1.

For example, in an organic light-emitting device according to an embodiment of the present invention, the organic layer may contain Compound 1 and may be, but is not limited to, an emissive layer, an electron transport layer and/or a hole-blocking layer.

An organic light-emitting device of the present invention may have one of a number of suitable structures. The organic light-emitting device may include an organic emissive layer between the first electrode and the second electrode. The device may further include at least one of a hole injection layer, a hole transport layer, an electron blocking layer, a hole-blocking layer, an electron transport layer and an electron injection layer in addition to the emissive layer.

Figure 1B:
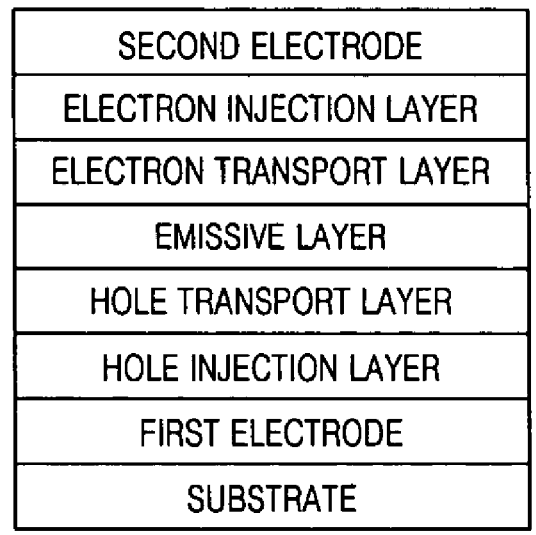
Figure 1C:
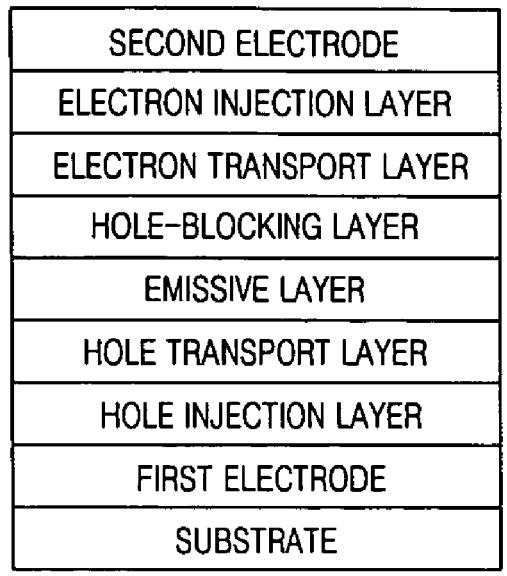

FIGS. 1A through 1C illustrate schematic sectional views of organic light-emitting devices according to embodiments of the present invention. The organic light-emitting device of FIG. 1A may have a first electrode/hole transport layer/emissive layer/electron transport layer/second electrode structure. The organic light-emitting device of FIG. 1B may have a first electrode/hole injection layer/hole transport layer/emissive layer/electron transport layer/electron injection layer/second electrode structure. The organic light-emitting device of FIG. 1C may have a first electrode/hole injection layer/hole transport layer/emissive layer/hole-blocking layer/electron transport layer/electron injection layer/second electrode structure. The emissive layer, the electron transport layer and/or the hole-blocking layer may include Compound 1.

The emissive layer of the organic light-emitting device according to embodiments of the present invention may include a colored dopant, e.g., a red, green, blue or white phosphorescent dopant, a red, green, blue or white fluorescent dopant, etc. The phosphorescent dopant may be an organic metal compound which contains, e.g., Ir, Pt, Os, Ti, Zr, Hf, Eu, Tb, Tm, etc.

Hereinafter, a method of manufacturing an organic light-emitting device according to an embodiment of the present invention will be described with reference to the organic light-emitting device illustrated in FIG. 1C.

First, a first electrode may be formed on a substrate by, e.g., depositing or sputtering a high work-function material on the substrate. The substrate may be a substrate that is typically used in organic light-emitting devices. The substrate may be, e.g., a glass substrate or a transparent plastic substrate that exhibits mechanical strength, thermal stability, transparency, surface smoothness, ease of treatment, and is waterproof. The first electrode may be, e.g., an anode. The material used to form the first electrode may be, e.g., ITO, IZO, $SnO_2$, ZnO, or a suitable transparent material that has high conductivity.

A hole injection layer (HIL) may be formed on the first electrode by, e.g., vacuum deposition, spin coating, casting, a Langmuir-Blodgett (LB) process, etc. When the HIL is formed by vacuum deposition, deposition conditions may vary according to the compound that is used to form the HIL, and the structure and thermal properties of the HIL to be formed. In general, however, conditions for vacuum deposition may include, e.g., a deposition temperature of about 50° C. to about 500° C., a pressure of about $10^{-8}$ torr to about $10^{-3}$ torr, a deposition speed of about 0.01 to about 100 Å/sec, and a layer thickness of about 10 Å to about 5 μm.

The material for the HIL may be, e.g., a phthalocyanine compound such as a copper phthalocyanine disclosed in U.S. Pat. No. 4,356,429, which is incorporated by reference herein in its entirety. The material for the HIL may also be, e.g., a star-burst type amine derivative such as TCTA, m-MTDATA, and m-MTDAPB, disclosed in Advanced Materials, vol. 6, issue 9, pp. 677-679 (1994), which is incorporated by reference herein in its entirety.

m-MTDATA refers to the compound represented by Structure 6, below:

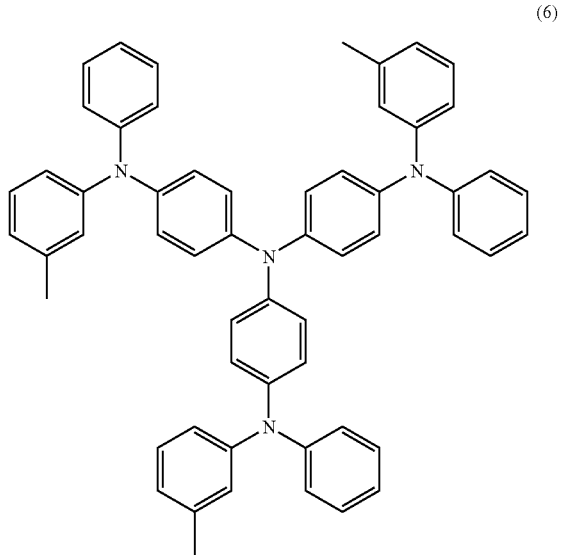

(6)

A hole transport layer (HTL) may be formed on the HIL by, e.g., vacuum deposition, spin coating, casting, LB, or the like. When the HTL is formed by vacuum deposition, conditions for deposition may be similar to those for formation of the HIL, although conditions for deposition may vary according to the compound that is used to form the HTL. The material used to form the HTL may be, e.g., any material that is typically used to form the HTL. The material may be, e.g., a carbazole derivative, such as N-phenylcarbazole, polyvinylcarbazole, or a typical amine derivative having an aromatic condensation ring, such as N,N'-bis(3-methylphenyl)-N,N'-diphenyl-[1,1-biphenyl]-4,4'-diamine (TPD), N,N'-di(naphthalene-1-yl)-N,N'-diphenyl benzidine (α-NPD), etc.

α-NPD refers to the compound represented by Structure 7, below:

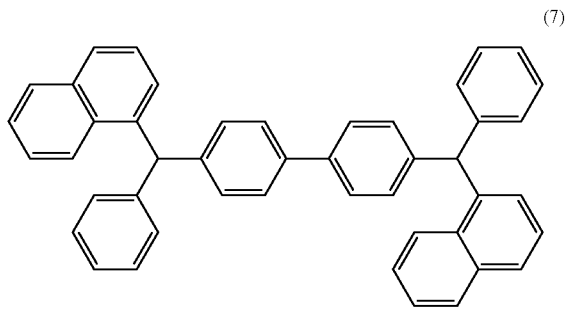

(7)

An emissive layer (EML) may be formed on the HTL by, e.g., vacuum deposition, spin coating, casting, LB, etc. When the EML is formed by vacuum deposition, conditions for deposition may be similar to those for formation of the HIL, although conditions for deposition may vary according to a material that is used to form the EML. The EML may be formed using a triazine-based compound according to the present invention, e.g., Compound 1.

For example, Compound 1 may be used for a phosphorescent host. A host material such as tris(8-quinolinorate)aluminum (Alq$_3$), 4,4'-N,N'-dicarbazole-biphenyl (CBP), or Compound 9, represented by Structure 9, below, may also be used to form the EML.

(9)

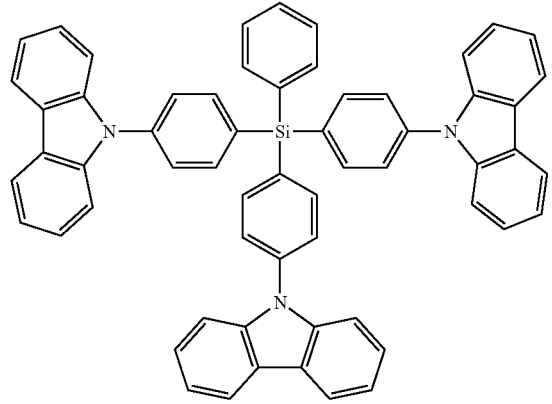

The EML may further include a colored dopant. Dopants may include, e.g., a fluorescent dopant such as IDE102 or IDE105 (Idemitsu Co.), C$_{545}$T (Hiyasibara Co.), etc, a phosphorescent dopant such as red phosphorescent dopant PtOEP or RD 61 (UDC Co.), green phosphorescent dopant Ir(PPy)$_3$ (where PPy is 2-phenylpyridine), blue phosphorescent dopant F2Irpic, Compound 8, represented by Structure 8, below, Compound 10, represented by Structure 10, below, etc. Compound 8 may be derived as set forth in U.S. Patent Publication No. 2003/0068526, which is incorporated by reference herein in its entirety.

(8)

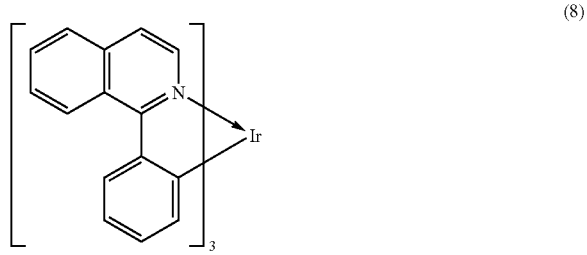

(10)

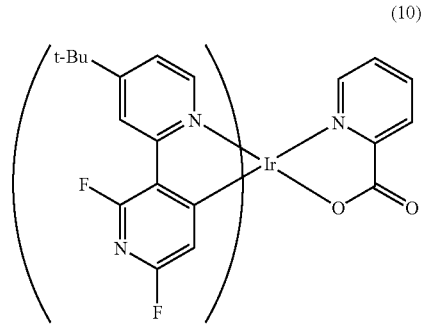

The concentration of the dopant may be, e.g., in the range of about 0.01 to about 15 parts by weight, based on 100 parts by weight of the host and dopant.

A hole-blocking layer (HBL) may be formed on the EML to prevent diffusion of triplet excitons or holes into an electron transport layer, which is described below, when the phosphorescent dopant is used to form the EML. The HBL may be formed by, e.g., deposition or spin coating. The material used to form the HBL may include, e.g., a triazine-based compound according to the present invention such as Compound 1, or another compound typically used for the HBL such as an oxadiazole derivative, a triazole derivative, a phenanthroline derivative, a hole-blocking material as disclosed in Japanese Patent Publication No. 11-329734, which is incorporated by reference herein in its entirety, BCP, Balq, etc.

An electron transport layer (ETL) may be formed by, e.g., vacuum deposition, spin coating, casting, etc. The material used to form the ETL may be, e.g., a triazine-based compound according to an embodiment of the present invention such as Compound 1, a quinoline derivative such as Alq$_3$, etc., or any suitable material that stably transports electrons injected from a cathode.

An electron injection layer (EIL) for allowing easy injection of electrons from a cathode may be formed on the ETL. The material that is used to form the EIL may be, e.g., LiF, NaCl, CsF, Li$_2$O, BaO, etc. Conditions for depositing the EIL may be similar to the conditions for formation of the HIL, although they may vary according to the material that is used to form the EIL.

A second electrode may be,formed on the EIL by, e.g., vacuum deposition, sputtering, etc. The second electrode may be, e.g., a cathode. The second electrode may be formed of a low work-function metal, an alloy, an electrically conductive compound, a combination of these, etc. Where a metal is employed, the metal may be, e.g., Li, Mg, Al, Al—Li, Ca, Mg—In, Mg—Ag, etc.

A transparent cathode may be used to produce a front surface light-emitting device, and may be formed of, e.g., ITO or IZO.

An organic light-emitting device according to an embodiment of the present invention may have the structure illustrated in FIG. 1C, i.e., first electrode/HIL/HTL/EML/HBL/ETL/EIL/second electrode. However, the structure of the organic light-emitting device according to the present invention may vary from that illustrated. For example, it may include one or two interlayers, etc.

EXAMPLE AND COMPARATIVE EXAMPLES

Hereinafter, the present invention will be described with reference to the following Examples and Comparative Examples. These examples are for illustrative purposes only and are not intended to limit the scope of the invention.

In particular, the present invention will be described with reference to: Synthesis Example 1, including the syntheses of Intermediates A and B, which details the synthesis of Compound 2, represented by Structure 2; Synthesis Example 2, including the syntheses of Intermediates C and D, which details the synthesis of Compound 3, represented by Structure 3; Synthesis Example 3, including the syntheses of Intermediates E and F, which details the synthesis of Compound 4, represented by Structure 4; and Synthesis Example 4, including the syntheses of Intermediates G and H, which details the synthesis of Compound 5, represented by Structure 5.

Also described below are Examples 1-4, which detail organic light-emitting devices according to embodiments of the present invention, wherein Compound 2 is employed as an electron transport layer, a hole-blocking layer and a host of an emissive layer, and Compound 5 is employed as a hole-blocking layer, respectively, as well as Comparative Examples A and B, which detail comparative organic light-emitting devices.

Synthesis Example 1

Compound 2, including Intermediates A and B

Compound 2 was synthesized through Reaction Scheme 2, below:

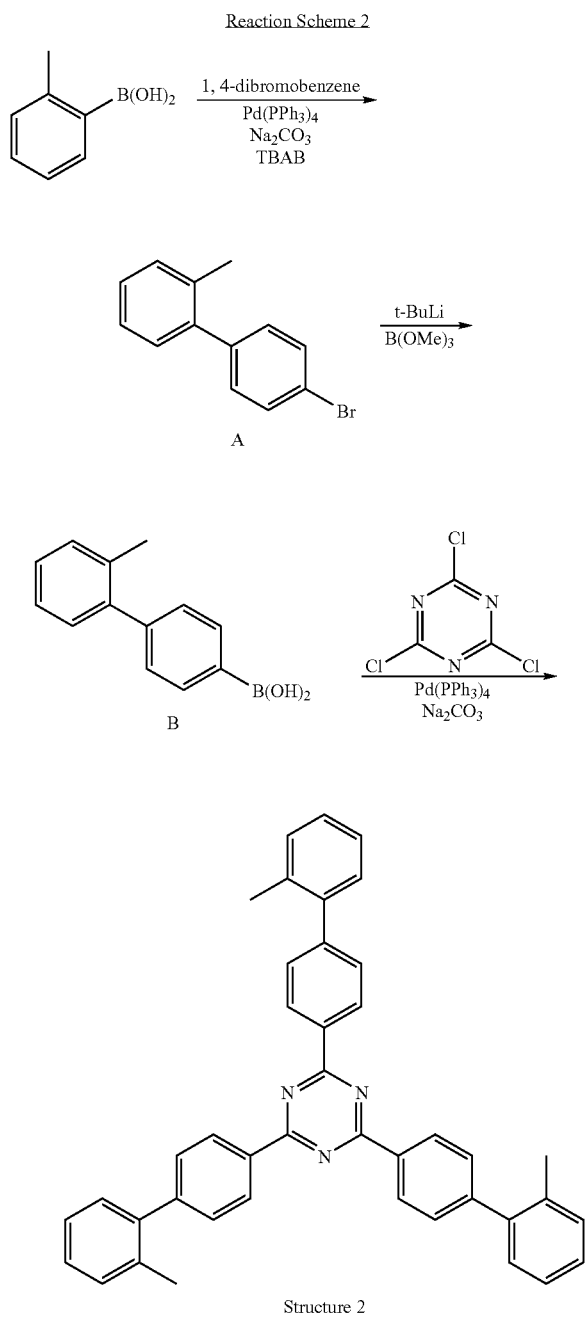

Structure 2

Synthesis of Intermediate A 5.7 g (41.9 mmol) of o-tolylboronic acid, 10 g (41.9 mmol) of 1,4-dibromobenzene, 0.315 g (0.273 mmol) of tetrakis(triphenylphosphine)palladium, 0.68 g (2.1 mmol) of tetrabutylammonium bromide and 42 mL of 2 M $Na_2CO_3$ were dissolved in 500 mL of toluene and stirred at a refluxing temperature for 5 hours. The reaction solution was cooled to room temperature, 200 mL of water was added to the solution and the organic layer was extracted three times with 200 mL of dichloromethane. The collected organic layer was dried over magnesium sulfate and the solvent was evaporated to obtain a crude product. The crude product was purified using silica gel column chromatography to produce 8.3 g of Intermediate A (88% yield).

Synthesis of Intermediate B 67 mL of 1.7 M tert-butyllithium dissolved in n-hexane was added dropwise to 7 g (28.3 mmol) of Intermediate A dissolved in THF at −78° C. and stirred for 20 minutes. 12.9 mL (113.3 mmol) of trimethoxy borate was added to the reaction solution, stirred at the same temperature for 2 hours and stirred at room temperature for 1 hour. The reaction solution was cooled to 0° C. and 200 mL of 6 N hydrochloric acid was added thereto, and the organic layer was extracted three times with 150 mL of diethylether. The collected organic layer was dried over magnesium sulfate and the solvent was evaporated to obtain a crude product. The crude product was purified using silica gel column chromatography to produce 4.04 g of Intermediate B (67% yield).

Synthesis of Compound 2

4 g (18.9 mmol) of Intermediate B, 0.87 g (4.72 mmol) of cyanuric chloride, 0.03 g (0.024 mmol) tetrakis(triphenylphosphine)palladium and 19 mL of 2 M $Na_2CO_3$ were dissolved in 100 mL of toluene and stirred at a refluxing temperature for 48 hours. The reaction mixture was cooled to room temperature, 200 mL of water was added thereto and the organic layer was extracted three times with 150 mL of diethylether. The collected organic layer was dried over magnesium sulfate and the solvent was evaporated to obtain a crude product. The crude product was recrystallized from dichloromethane and methyl alcohol to produce 1.33 g of Compound 2, represented by Structure 2 (48% yield).

$^1$H NMR ($CDCl_3$, 400 MHz) δ (ppm) 8.86 (dd, 6H), 7.56 (dd, 6H), 7.35~7.29 (m, 12H), 2.35 (s, 9H).

In a UV spectrum measurement, the maximum absorption wavelength of 0.2 mM Compound 2 (in $CHCl_3$) was 300.5 nm.

Figure 2:
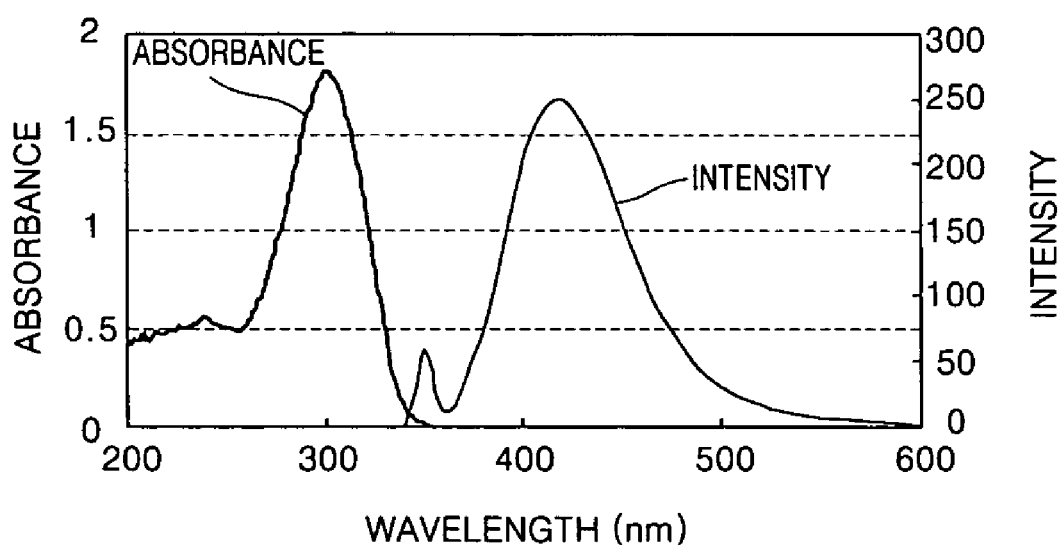
FIG. 2 illustrates a photoluminescence spectrum of exemplary Compound 2 according to an embodiment of the present invention.

Photoluminescence (PL) of 10 mM Compound 2 (in $CHCl_3$) was measured at 350 nm. The maximum emission was observed at a wavelength of 420 nm (refer to FIG. 2).

Figure 3:
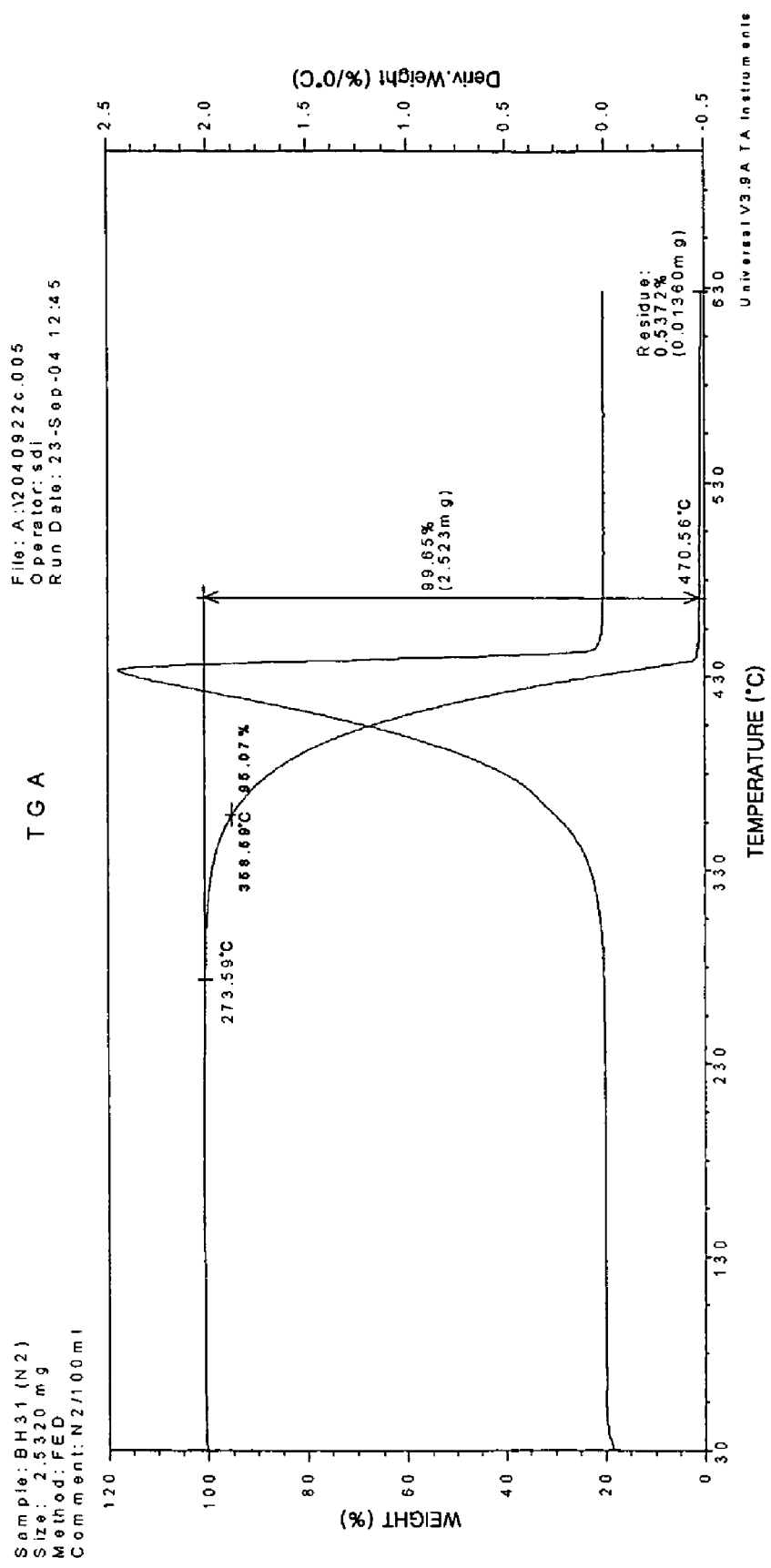
FIG. 3 illustrates results of a thermo gravimetric analysis of exemplary Compound 2 according to an embodiment of the present invention.
Figure 4:
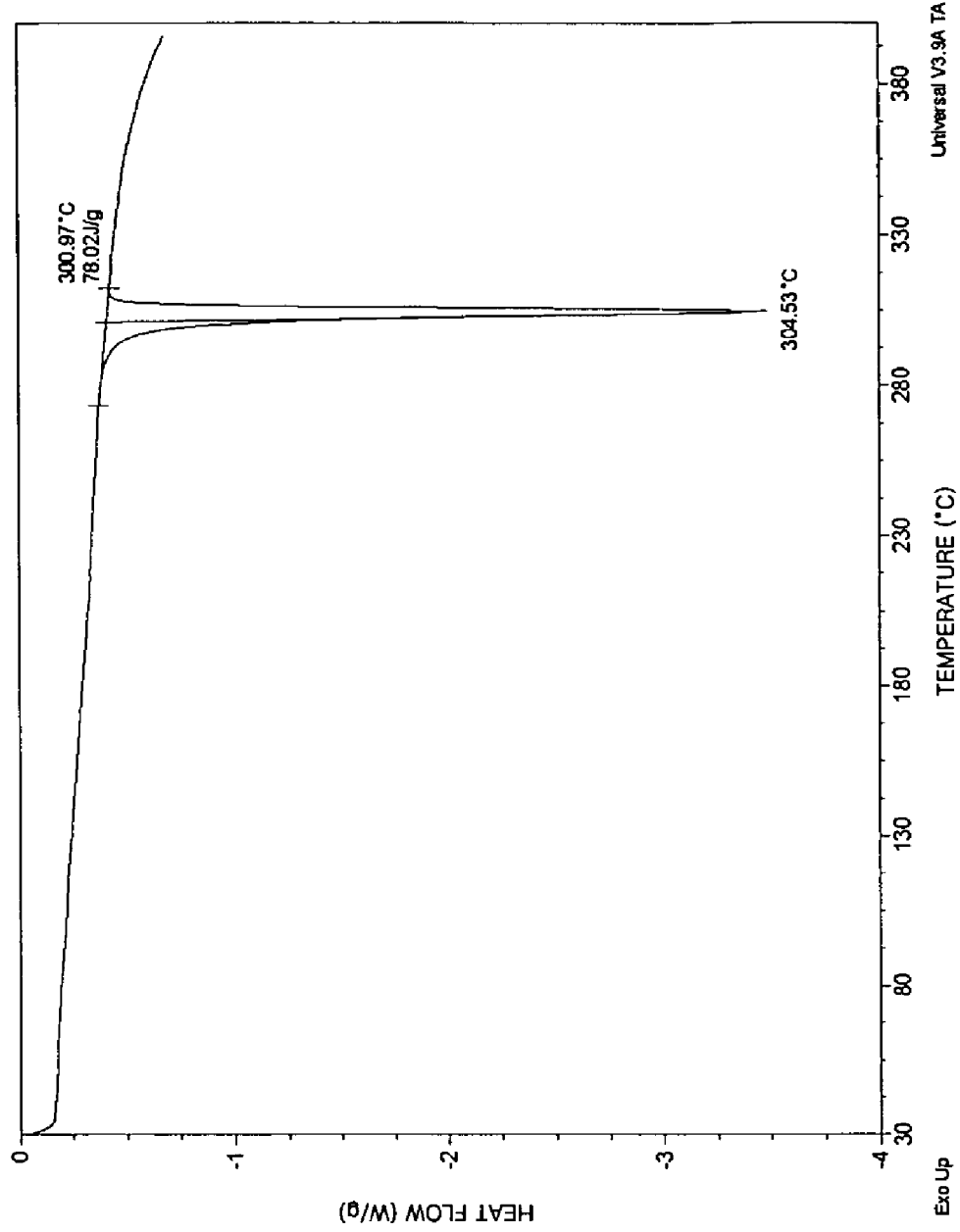
FIG. 4 illustrates results of a differential scanning calorimetry analysis of exemplary Compound 2 according to an embodiment of the present invention.

Thermal analysis for Compound 2 was performed using thermo gravimetric analysis (TGA) and differential scanning calorimetry (DSC) under the following conditions: $N_2$ atmosphere; temperatures for TGA: room temperature to 600° C. (10° C./min); temperatures for DSC: room temperature to 400° C.; pan type for TGA: Pt pan in disposable Al pan; pan type for DSC: disposable Al pan. The results of the thermal analysis were: Td was 359° C. and the melting point (Tm) was 305° C. (refer to FIGS. 3 and 4).

Synthesis Example 2

Compound 3, Including Intermediates C and D

Compound 3 was synthesized through Reaction Scheme 3, below:

Reaction Scheme 3

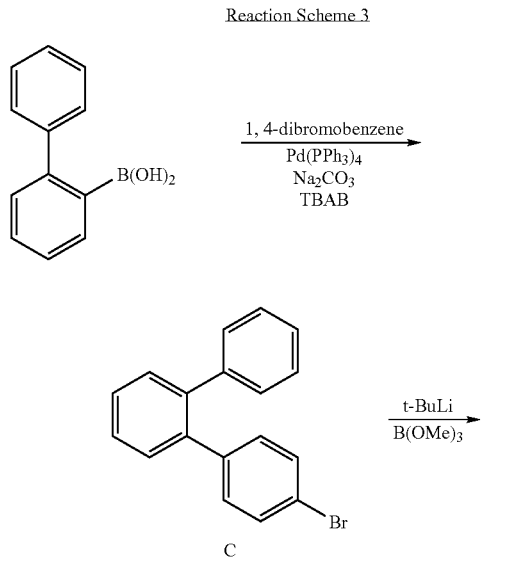

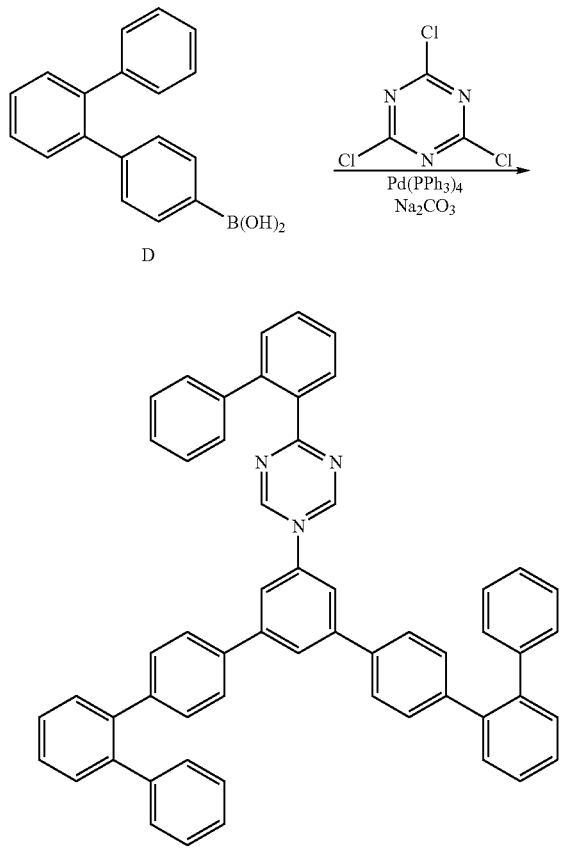

Structure 3

Synthesis of Intermediate C 10.93 g of Intermediate C (77% yield) was obtained in the same manner as Intermediate A in Synthesis Example 1, above, except that 10 g (50.50 mmol) of 2-biphenyl boronic acid was used instead of o-tolylboronic acid.

Synthesis of Intermediate D 6.92 g of Intermediate D (71% yield) was obtained in the same manner as Intermediate B in Synthesis Example 1, above, except that 11 g (35.58 mmol) of Intermediate C was used instead of Intermediate A.

Synthesis of Compound 3

2.54 g of Compound 3 (56% yield) was obtained in the same manner as Compound 2 in Synthesis Example 1, above, except that 6.5 g (23.71 mmol) of Intermediate D was used instead of Intermediate B.

$^1$H NMR (CDCl$_3$, 400 MHz) δ (ppm) 8.58 (d, 6H), 7.51~7.46 (m, 12H), 7.33 (d, 6H), 7.26~7.18 (m, 15H)

Figure 5:
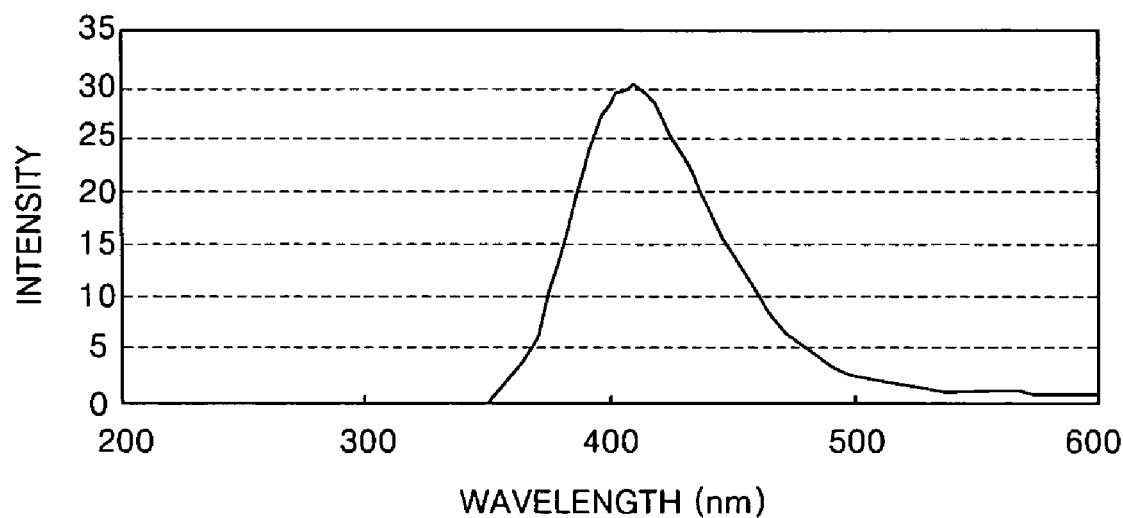
FIG. 5 illustrates a photoluminescence spectrum of exemplary Compound 3 according to an embodiment of the present invention.

PL of 10 mM Compound 3 (in CHCl$_3$) was measured at 360 nm. The maximum emission was observed at a wavelength of 410 nm (see FIG. 5).

Synthesis Example 3

Compound 4, Including Intermediates E and F

Compound 4 was synthesized through Reaction Scheme 4, below:

Reaction Scheme 4

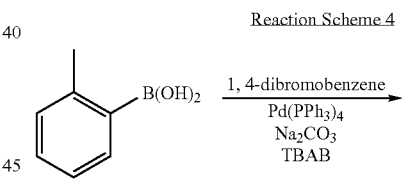

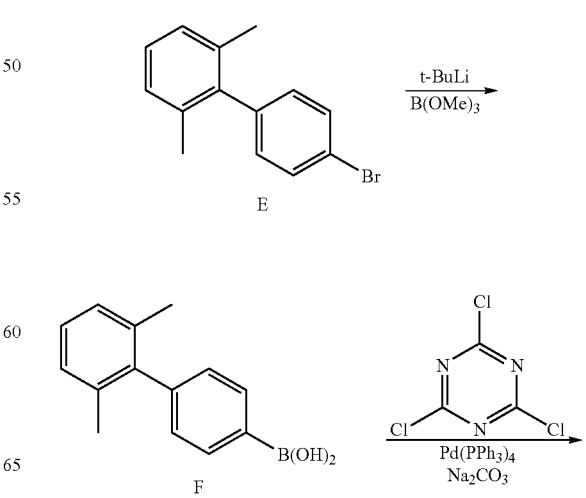

E

F

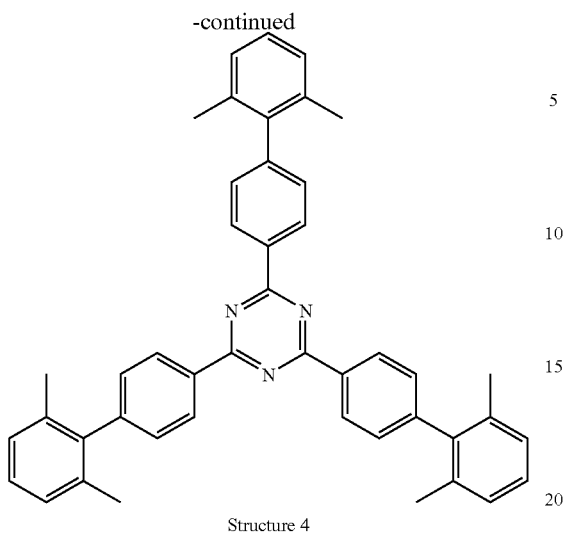

Structure 4

Synthesis of Intermediate E 7.61 g of Intermediate E (83% yield) was obtained in the same manner as Intermediate A in Synthesis Example 1, above, except that 7 g (46.64 mmol) of 2,6-dimethylphenyl boronic acid was used instead of o-tolylboronic acid.

Synthesis of Intermediate F 5.85 g of Intermediate F (70% yield) was obtained in the same manner as Intermediate B in Synthesis Example 1, above, except that 8 g (37.01 mmol) of Intermediate E was used instead of Intermediate A.

Synthesis of Compound 4

1.97 g of Compound 4 (52% yield) was obtained in the same manner as Compound 2 in Synthesis Example 1, above, except that 5.5 g (24.33 mmol) of Intermediate F was used instead of Intermediate B.

$^1$H NMR (CDCl$_3$, 400 MHz) δ (ppm) 8.91 (d, 6H), 7.40 (d, 6H), 7.21~7.14 (m, 9H), 2.10 (s, 18H).

Figure 6:
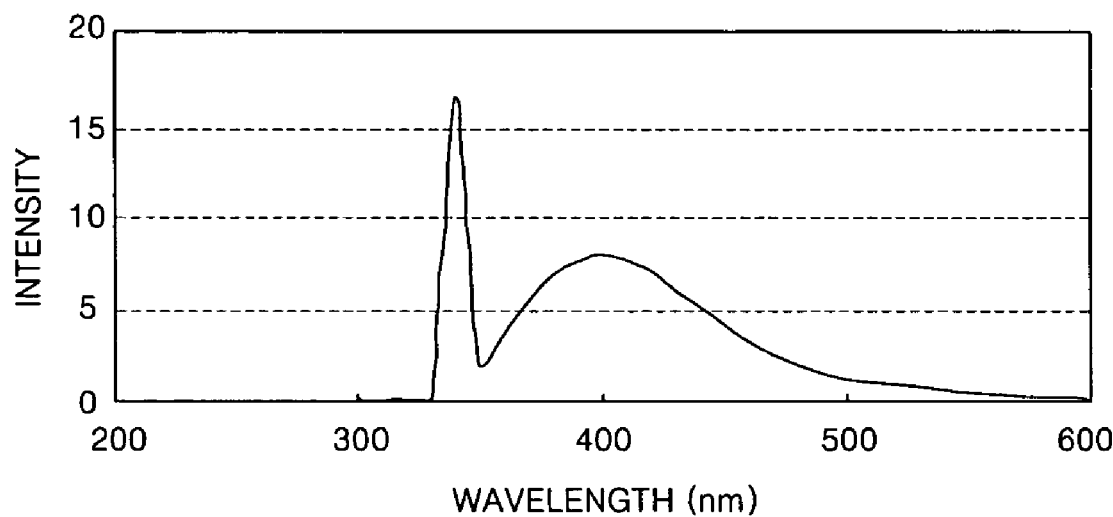
FIG. 6 illustrates a photoluminescence spectrum of exemplary Compound 4 according to an embodiment of the present invention.

PL of 10 mM Compound 4 (in CHCl$_3$) was measured at 360 nm. The maximum emission was observed at a wavelength of 400 nm (see FIG. 6).

Synthesis Example 4

Compound 5, Including Intermediates G and H

Compound 5 was synthesized through Reaction Scheme 5, below:

Reaction Scheme 5

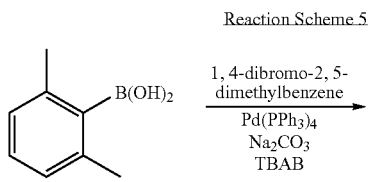

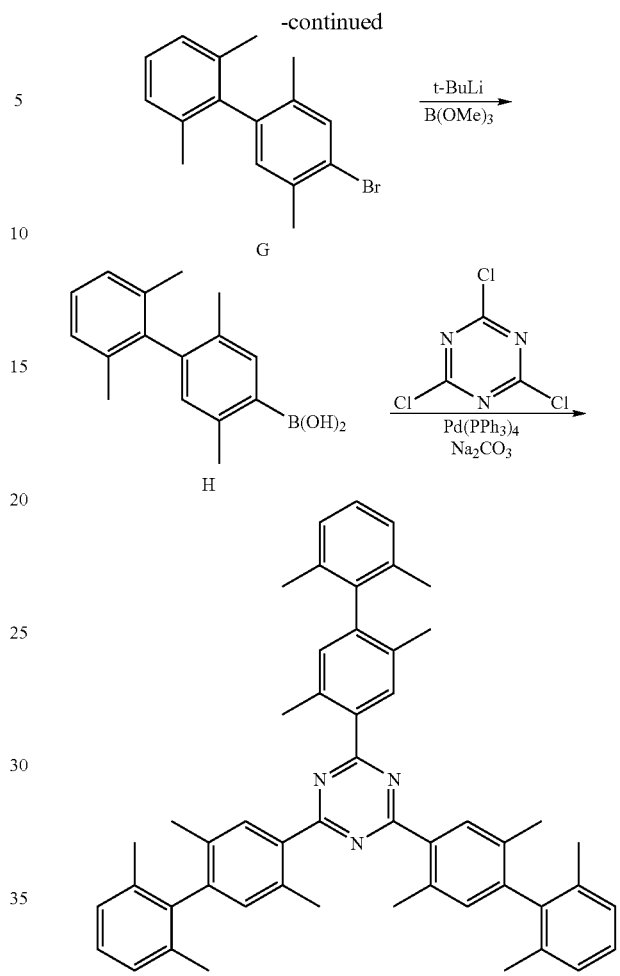

Structure 5

Synthesis of Intermediate G 9.81 g of Intermediate G (55% yield) was obtained in the same manner as Intermediate A in Synthesis Example 1, above, except that 10.3 g (68.40 mmol) of 2,6-dimethylphenyl boronic acid was used instead of o-tolylboronic acid and 16.4 g (62.18 mmol) of 1,4-dibromo-2,5-dimethylbenzene was used instead of 1,4-dibromobenzene.

$^1$H NMR (CDCl$_3$, 400 MHz) δ (ppm) 7.42 (s, 1H), 7.09~7.03 (m, 3H), 6.86 (s, 1H), 2.35 (s, 3H), 1.91 (s, 3H), 1.88 (s, 6H); $^{13}$C NMR (CDCl$_3$, 400 MHz) δ (ppm) 140.57, 136.28, 135.94, 135.89, 134.19, 131.85, 127.98, 127.85, 123.76, 22.97, 20.93, 19.25.

Synthesis of Intermediate H 5.68 g of Intermediate H (68% yield) was obtained in the same manner as Intermediate B in Synthesis Example 1, above, except that 9.5 g (32.85 mmol) of Intermediate G was used instead of Intermediate A.

$^1$H NMR (CDCl$_3$, 400 MHz) δ (ppm) 8.18 (s, 1H), 7.18~7.12 (m, 3H), 6.98 (s, 1H), 2.85 (s, 3H), 2.03 (s, 3H), 2.00 (s, 6H); $^{13}$C NMR (CDCl$_3$, 400 MHz) δ (ppm) 144.79, 143.84, 140.84, 139.14, 135.59, 135.50, 132.23, 131.14, 127.24, 127.00, 22.64, 20.35, 19.01.

Synthesis of Compound 5

2.33 g of Compound 5 (61% yield) was obtained in the same manner as Compound 2 in Synthesis Example 1, above, except that 5.5 g (21.64 mmol) of Intermediate H was used instead of Intermediate B.

$^1$H NMR (CDCl$_3$, 400 MHz) δ (ppm) 8.14 (s, 3H), 7.21~7.12 (m, 9H), 7.05 (s, 3H), 2.81 (s, 9H), 2.06 (s, 9H), 2.01 (s, 18H); $^{13}$C NMR (CDCl$_3$, 400 MHz) δ (ppm) 143.56, 140.44, 136.29, 135.66, 135.02, 133.54, 132.83, 132.31, 127.26, 127.11, 29.70, 21.69, 20.41, 19.05.

In UV spectrum measurement, the maximum absorption wavelength of 0.2 mM Compound 5 (in CHCl$_3$) was 282.5 nm.

Figure 7:
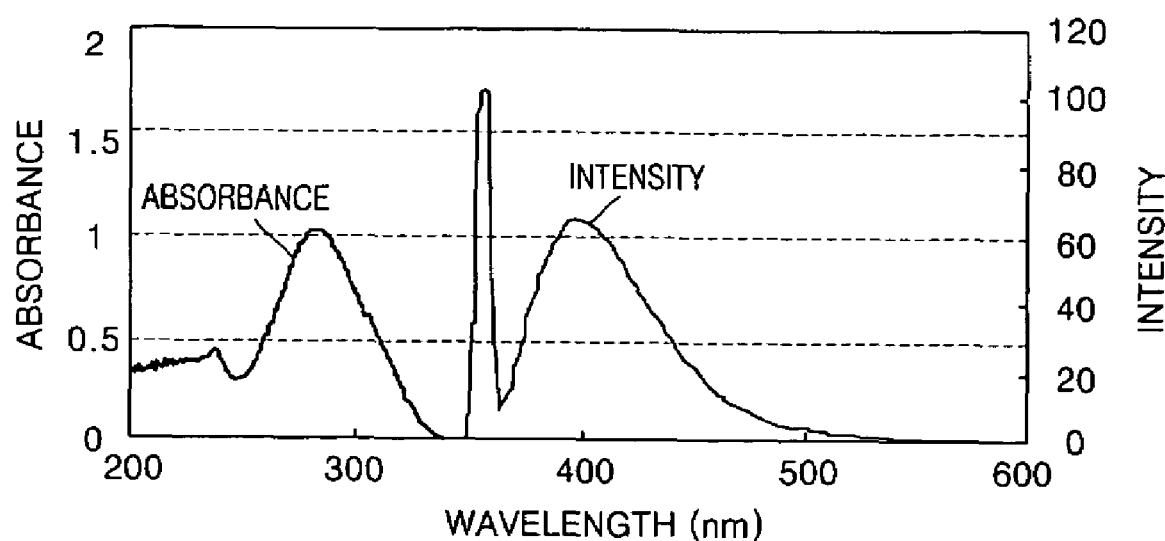
FIG. 7 illustrates a photoluminescence spectrum of exemplary Compound 5 according to an embodiment of the present invention.

PL of 10 mM Compound 5 (in CHCl$_3$) was measured at 356 nm. The maximum emission was observed at a wavelength of 397 nm (see FIG. 7).

Figure 8:
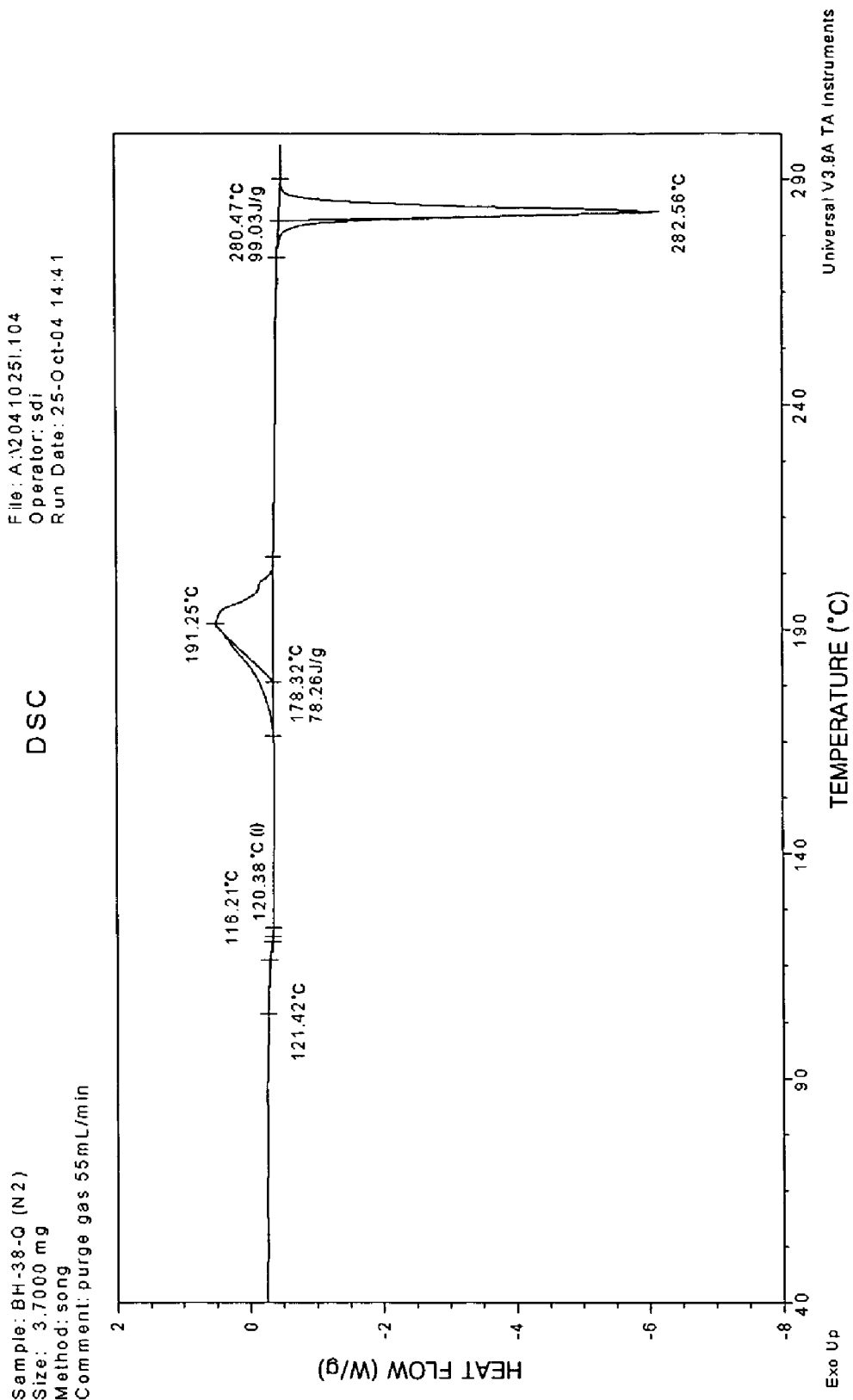
FIG. 8 illustrates results of a thermo gravimetric analysis of exemplary Compound 5 according to an embodiment of the present invention.
Figure 9:
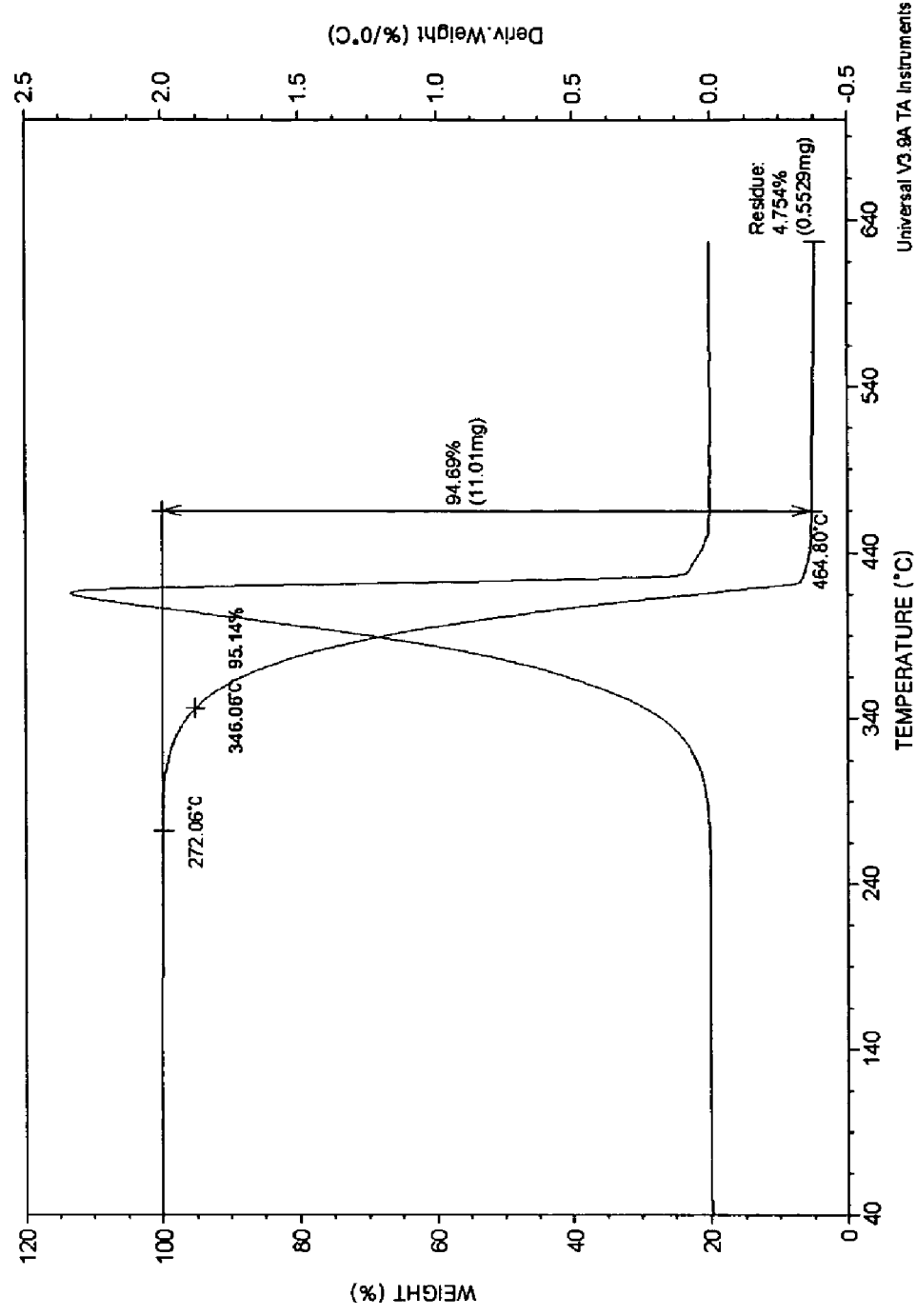
FIG. 9 illustrates results of a differential scanning calorimetric analysis of exemplary Compound 5 according to an embodiment of the present invention.

Thermal analysis for Compound 5 was carried out using TGA and DSC under the following conditions: N$_2$ atmosphere; temperatures for TGA: room temperature to 600° C. (10° C./min); temperatures for DSC: room temperature to 400° C.; pan type for TGA: Pt pan in disposable Al pan; pan type for DSC: disposable Al pan. The results of the thermal analysis were: Tg was 120° C., Tc was 191° C., and Tm was 283° C. (refer to FIGS. 8 and 9).

Example 1

Compound 2 as an Electron Transport Layer

An organic light-emitting device having the following structure was fabricated: m-MTDATA (750 Å)/α-NPD (150 Å)/CBP (300 Å):Compound 8 represented by Structure 8 (10%)/Balq (50 Å)/Compound 2 (200 Å)/LiF (80 Å)/Al (3,000 Å). Compound 2, as synthesized in Synthesis Example 1, above, was used as an ETL.

In detail, a 15 Ω/cm$^2$ (1,200 Å) ITO glass substrate (Corning Co.), was cut to a size of 50 mm×50 mm×0.7 mm, microwave washed with isopropyl alcohol for 5 minutes, microwave washed with pure water for 5 minutes, and washed with UV ozone for 30 minutes. m-MTDATA was vacuum deposited on the substrate to form a HIL with a thickness of 750 Å. α-NPD was vacuum deposited on the HIL to form a HTL with a thickness of 150 Å. CBP as a phosphorescent host and 10% of Compound 8 as a phosphorescent dopant were vacuum deposited on the HTL to form an EML with a thickness of 300 Å. Balq was vacuum deposited on the EML to form a HBL with a thickness of 50 Å. Compound 2 was vacuum deposited on the HBL to form an ETL with a thickness of 200 Å. LiF was vacuum deposited on the ETL to form an EIL with a thickness of 80 Å and Al was vacuum deposited on the EIL to form a cathode with a thickness of 3,000 Å. As a result, an organic light-emitting device having a structure as shown in FIG. 1C was fabricated. This organic light-emitting device will be referred to as Example 1.

Example 2

Compound 2 as a Hole-Blocking Layer

An organic light-emitting device having the following structure was fabricated: m-MTDATA (750 Å)/α-NPD (150 Å)/CBP (300 Å):Compound 8 (10%)/Compound 2 (50 Å)/Alq$_3$ (200 Å)/LiF (80 Å)/Al (3,000 Å). Compound 2, as synthesized in Synthesis Example 1, above, was used as a HBL.

In detail, a 15 Ω/cm$^2$ (1,200 Å) ITO glass substrate (Corning Co.), was cut to a size of 50 mm×50 mm×0.7 mm, microwave washed with isopropyl alcohol for 5 minutes, microwave washed with pure water for 5 minutes, and washed with UV ozone for 30 minutes. m-MTDATA was vacuum deposited on the substrate to form a HIL with a thickness of 750 Å. α-NPD was vacuum deposited on the HIL to form a HTL with a thickness of 150 Å. CBP as a phosphorescent host and 10% of Compound 8 as a phosphorescent dopant were vacuum deposited on the HTL to form an EML with a thickness of 300 Å. Compound 2 was vacuum deposited on the EML to form a HBL with a thickness of 50 Å. Alq$_3$ was vacuum deposited on the HBL to form an ETL with a thickness of 200 Å. LiF was vacuum deposited on the ETL to form an EIL with a thickness of 80 Å and Al was vacuum deposited on the EIL to form a cathode with a thickness of 3,000 Å. As a result, an organic light-emitting device having a structure as shown in FIG. 1C was fabricated. This organic light-emitting device will be referred to as Example 2.

Example 3

Compound 2 as a Host of the Emissive Layer

An organic light-emitting device having the following structure was fabricated: m-MTDATA (750 Å)/α-NPD (150 Å)/Compound 2:Ir(PPy)$_3$ (6%) (300 Å)/Balq (50 Å)/Alq$_3$ (200 Å)/LiF (80 Å)/Al (3,000 Å). Compound 2, as synthesized in Synthesis Example 1, above, was used as a host of the emissive layer.

In detail, a 15 Ω/cm$^2$ (1,200 Å) ITO glass substrate (Corning Co.), was cut to a size of 50 mm×50 mm×0.7 mm, microwave washed with isopropyl alcohol for 5 minutes, microwave washed with pure water for 5 minutes, and washed with UV ozone for 30 minutes. m-MTDATA was vacuum deposited on the substrate to form a HIL with a thickness of 750 Å. α-NPD was vacuum deposited on the HIL to form a HTL with a thickness of 150 Å. Compound 2 as a phosphorescent host and 6% of Ir(PPy)$_3$ as a phosphorescent dopant were vacuum deposited on the HTL to form an EML with a thickness of 300 Å. Balq was vacuum deposited on the EML to form a HBL with a thickness of 50 Å. Alq$_3$ was vacuum deposited on the HBL to form an ETL with a thickness of 200 Å. LiF was vacuum deposited on the ETL to form an EIL with a thickness of 80 Å and Al was vacuum deposited on the EIL to form a cathode with a thickness of 3,000 Å. As a result, an organic light-emitting device having a structure as shown in FIG. 1C was fabricated. This organic light-emitting device will be referred to as Example 3.

Example 4

Compound 5 as a Hole-Blocking Layer

An organic light-emitting device having the following structure was fabricated: m-MTDATA (750 Å)/α-NPD (150 Å)/Compound 9:Compound 10 (10%) (300 Å)/Compound 5 (50 Å)/Alq$_3$ (200 Å)/LiF (80 Å)/Al (3,000 Å). Compound 5, as synthesized in Synthesis Example 4, above, was used as a material for the HBL.

In detail, a 15 Ω/cm$^2$ (1,200 Å) ITO glass substrate (Corning Co.), was cut to a size of 50 mm×50 mm×0.7 mm, microwave washed with isopropyl alcohol for 5 minutes, microwave washed with pure water for 5 minutes, and washed with UV ozone for 30 minutes. m-MTDATA was vacuum deposited on the substrate to form a HIL with a thickness of 750 Å. α-NPD was vacuum deposited on the HIL to form a HTL with a thickness of 150 Å. Compound 9 as a phosphorescent host and 10% of Compound 10 as a phosphorescent dopant were vacuum deposited on the HTL to form an EML with a thickness of 300 Å. Compound 5 was vacuum deposited on the EML to form a HBL with a thickness of 50 Å. $Alq_3$ was vacuum deposited on the HBL to form an ETL with a thickness of 200 Å. LiF was vacuum deposited on the ETL to form an EIL with a thickness of 80 Å and Al was vacuum deposited on the EIL to form a cathode with a thickness of 3,000 Å. As a result, an organic light-emitting device having a structure as shown in FIG. 1C was fabricated. This organic light-emitting device will be referred to as Example 4.

Comparative Example A

An organic light-emitting device having the following structure was fabricated: m-MTDATA (750 Å)/α-NPD (150 Å)/CBP (300 Å):Compound 8 (10%)/Balq (50 Å)/$Alq_3$ (200 Å)/LiF (80 Å)/Al (3,000 Å).

In detail, a 15 Ω/$cm^2$ (1,200 Å) ITO glass substrate (Corning Co.), was cut to a size of 50 mm×50 mm×0.7 mm, microwave washed with isopropyl alcohol for 5 minutes, microwave washed with pure water for 5 minutes, and washed with UV ozone for 30 minutes. m-MTDATA was vacuum deposited on the substrate to form a HIL with a thickness of 750 Å. α-NPD was vacuum deposited on the HIL to form a HTL with a thickness of 150 Å. CBP as a phosphorescent host and 10% of Compound 8 as a phosphorescent dopant were vacuum deposited on the HTL to form an EML with a thickness of 300 Å. Balq was vacuum deposited on the EML to form a HBL with a thickness of 50 Å. $Alq_3$ was vacuum deposited on the HBL to form an ETL with a thickness of 200 Å. LiF was vacuum deposited on the ETL to form an EIL with a thickness of 80 Å and Al was vacuum deposited on the EIL to form a cathode with a thickness of 3,000 Å. As a result, an organic light-emitting device having a structure as shown in FIG. 1C was fabricated. This organic light-emitting device will be referred to as Example A.

Comparative Example B

An organic light-emitting device having the following structure was fabricated: m-MTDATA (750 Å)/α-NPD (150 Å)/Compound 9:Compound 10 (10%) (300 Å)/BCP (50 Å)/$Alq_3$ (200 Å)/LiF (80 Å)/Al (3,000 Å).

In detail, a 15 Ω/$cm^2$ (1,200 Å) ITO glass substrate (Corning Co.), was cut to a size of 50 mm×50 mm×0.7 mm, microwave washed with isopropyl alcohol for 5 minutes, microwave washed with pure water for 5 minutes, and washed with UV ozone for 30 minutes. m-MTDATA was vacuum deposited on the substrate to form a HIL with a thickness of 750 Å. α-NPD was vacuum deposited on the HIL to form a HTL with a thickness of 150 Å. Compound 9 as a phosphorescent host and 10% of Compound 10 as a phosphorescent dopant were vacuum deposited on the HTL to form an EML with a thickness of 300 Å. BCP was vacuum deposited on the EML to form a HBL with a thickness of 50 Å. $Alq_3$ was vacuum deposited on the HBL to form an ETL with a thickness of 200 Å. LiF was vacuum deposited on the ETL to form an EIL with a thickness of 80 Å and Al was vacuum deposited on the EIL to form a cathode with a thickness of 3,000 Å. As a result, an organic light-emitting device having a structure as shown in FIG. 1C was fabricated. This organic light-emitting device will be referred to as Example B.

Analysis 1

Current-voltage, luminance, efficiency and power consumption of Examples 1 and 2, as well as Comparative Example A, were measured and the results are illustrated in FIGS. 10, 11, 12 and 13, respectively. Current-voltage, luminance, efficiency and power consumption of Example 4 and Comparative Example B were measured and the results are illustrated in FIGS. 14, 15, 16 and 17, respectively. Keithley and PhotoResearch (PR650) instruments were used to measure current-voltage and luminance (IVL), efficiency and power consumption properties. The turn-on voltage, driving voltage, current density, luminance, current efficiency, power efficiency and color coordinates of Comparative Example B and Example 4 are shown in Table 1, below.

TABLE 1

|  |  | Comp. Example B | Example 4 |
|---|---|---|---|
| Turn-on voltage (V) |  | 5 | 5 |
| Driving Voltage (V) |  | 8 | 8 |
| Current Density ($mA/cm^2$) |  | 2.265375 | 6.589 |
| Luminance ($cd/m^2$) |  | 102.7 | 672.4 |
| Current efficiency (cd/A) |  | 4.533466 | 10.20489 |
| Power efficiency (lm/W) |  | 1.780288 | 4.00745 |
| Color coordinates | x | 0.1485 | 0.1502 |
|  | y | 0.1701 | 0.1585 |

Figure 10:
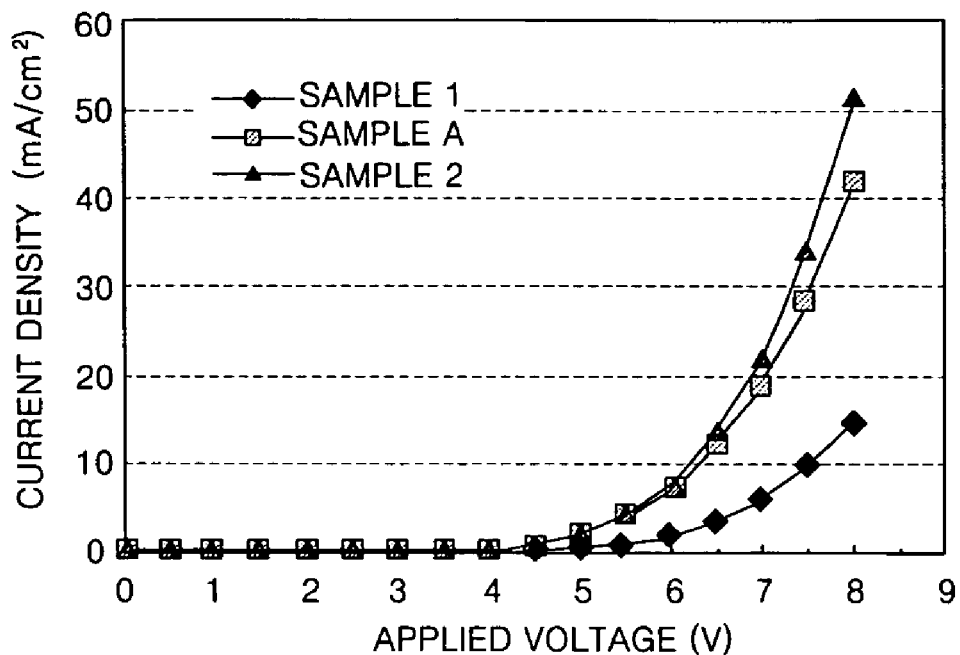
FIG. 10 illustrates a graph of current density as a function of applied voltage for organic light-emitting device Examples 1 and 2 according to embodiments of the present invention, and for Comparative Example A.
Figure 14:
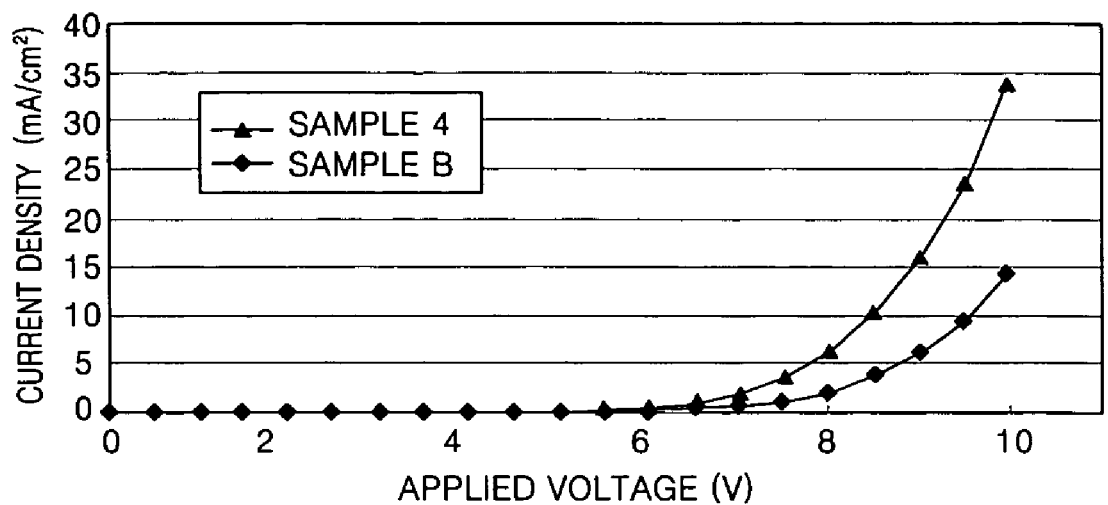
FIG. 14 illustrates a graph of current density as a function of applied voltage for organic light-emitting device Example 4 according to an embodiment of the present invention, and for Comparative Example B.

Referring to FIGS. 10 and 14, Examples 1 and 2 have a higher current density than Comparative Example A, and Example 4 has a higher current density than Comparative Example B when the same voltage is applied. Therefore, an organic light-emitting device according to the present invention may exhibit excellent current density.

Figure 11:
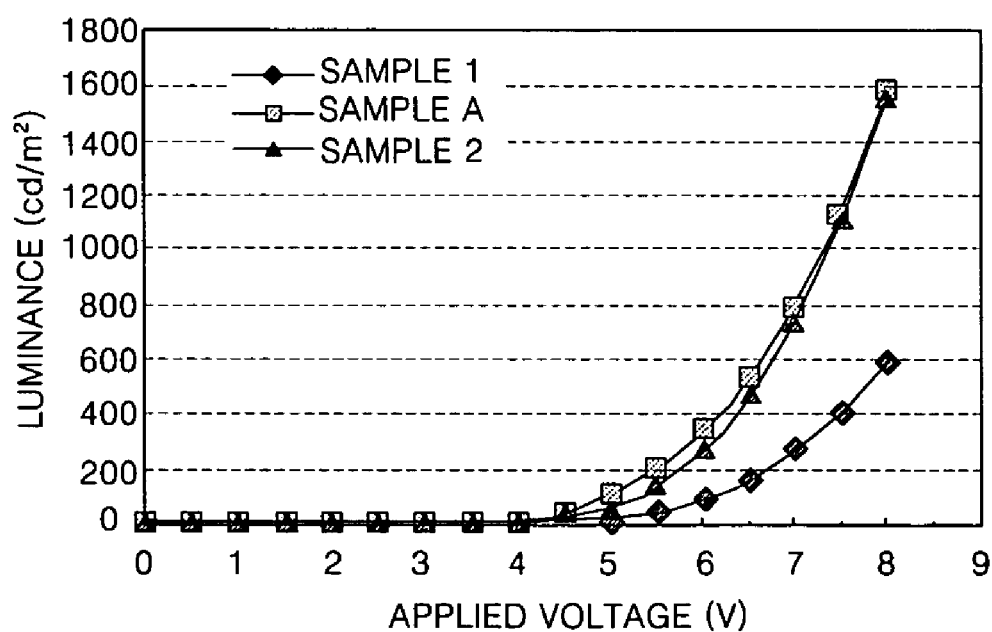
FIG. 11 illustrates a graph of luminance as a function of applied voltage for organic light-emitting device Examples 1 and 2 according to embodiments of the present invention, and for Comparative Example A.
Figure 15:
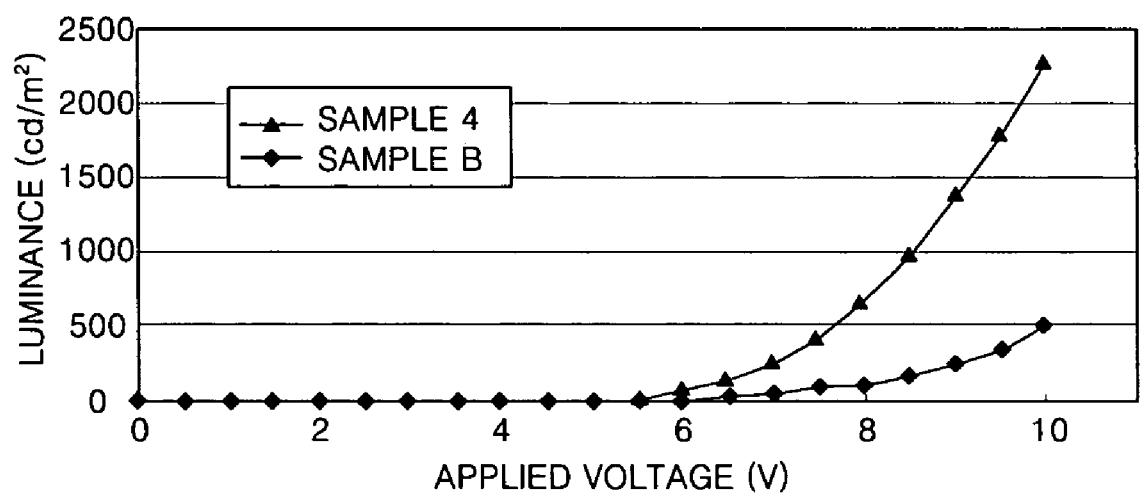
FIG. 15 illustrates a graph of luminance as a function of applied voltage for organic light emitting device Example 4 according to an embodiment of the present invention, and for Comparative Example B.

Referring to FIGS. 11 and 15, Examples 1 and 2 have a higher luminance than Comparative Example A, and Example 4 has a five times (5×) higher luminance than Comparative Example B when the same voltage is applied. Therefore, an organic light-emitting device according to the present invention may exhibit excellent luminance.

Figure 12:
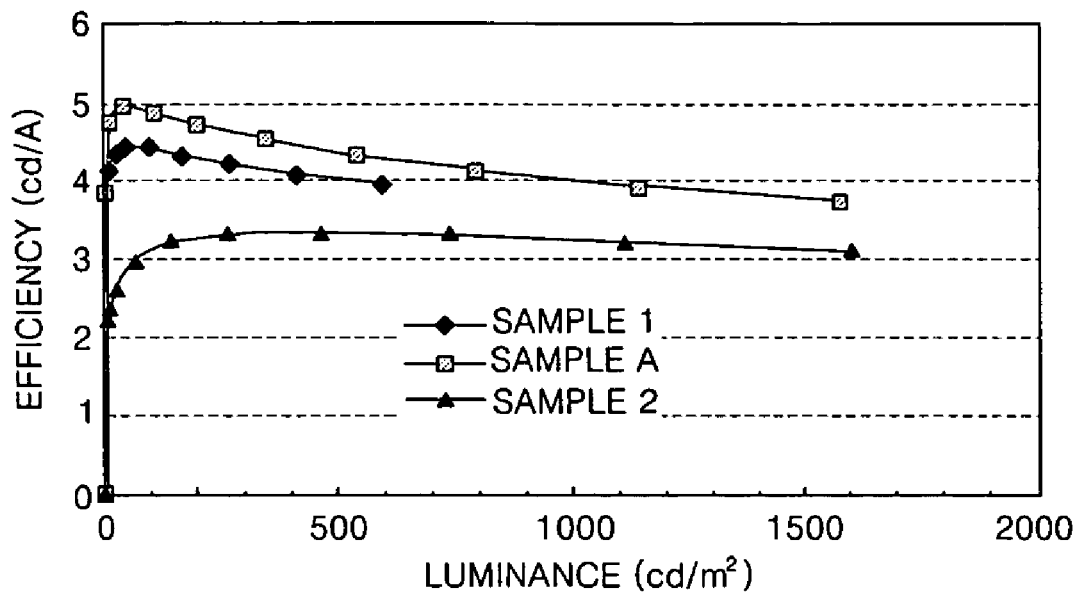
FIG. 12 illustrates a graph of efficiency as a function of luminance for organic light-emitting device Examples 1 and 2 according to embodiments of the present invention, and for Comparative Example A.
Figure 16:
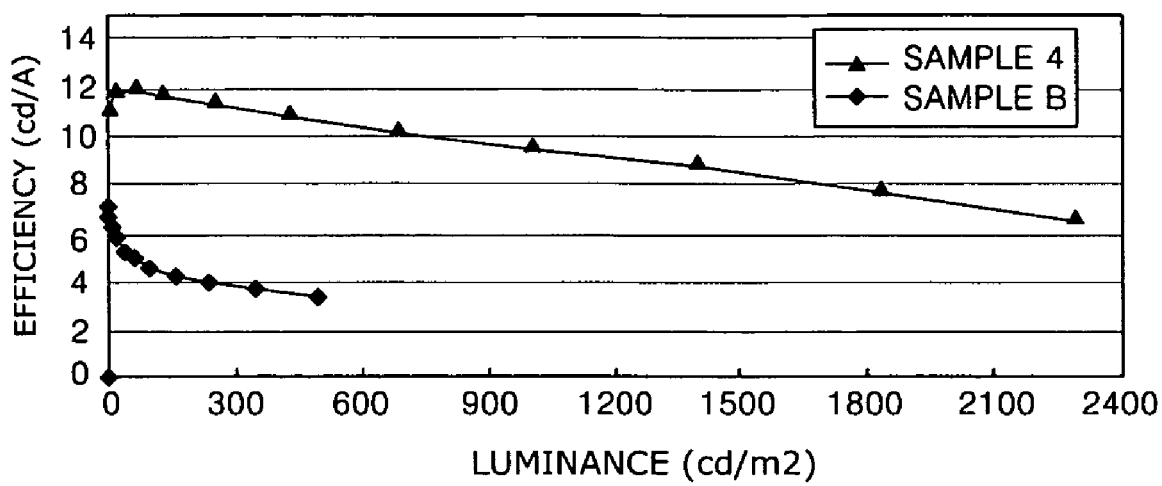
FIG. 16 illustrates a graph of efficiency as a function of luminance for organic light-emitting device Example 4 according to an embodiment of the present invention, and for Comparative Example B.

Referring to FIGS. 12 and 16, Examples 1 and 2 have a higher efficiency than Comparative Example A, and Example 4 has a higher efficiency than Comparative Example B. Therefore, an organic light-emitting device according to the present invention may exhibit excellent efficiency.

Figure 13:
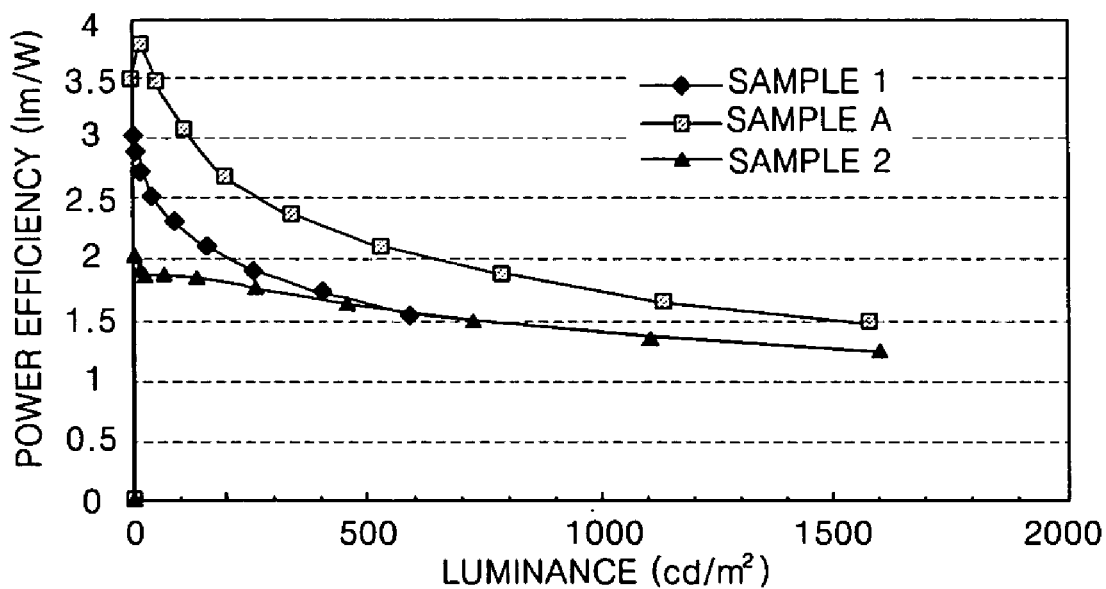
FIG. 13 illustrates a graph of power efficiency as a function of luminance for of organic light-emitting device Examples 1 and 2 according to embodiments of the present invention, and for Comparative Example A.
Figure 17:
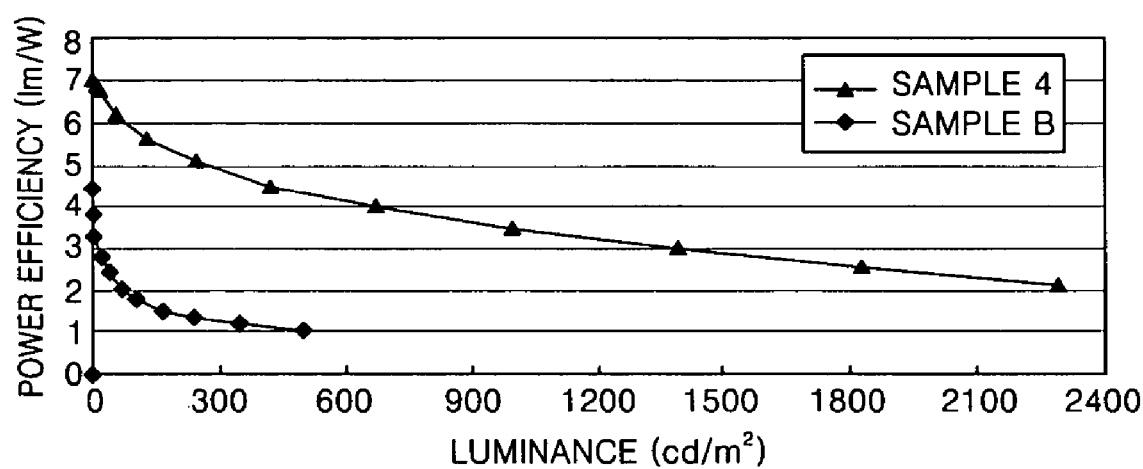
FIG. 17 illustrates a graph of power efficiency as a function of luminance for organic light-emitting devices Example 4 according to an embodiment of the present invention, and for Comparative Example B.

Referring to FIGS. 13 and 17, Examples 1 and 2 have a higher power efficiency than Comparative Example A, and Example 4 has a higher power efficiency than Comparative Example B. Therefore, an organic light-emitting device according to the present invention may exhibit excellent power efficiency.

In addition, as illustrated in Table 1, above, the turn-on voltage, driving voltage, current density, luminance, current efficiency, power efficiency and color coordinates of Example 4 may be superior to those of Comparative Example B.

Therefore, an organic light-emitting device according to an embodiment of the present invention may exhibit excellent electron transport and hole-blocking capabilities.

Analysis 2

The luminance, current efficiency, power efficiency and lifespan of Example 3 were measured in the same manner as Analysis 1. The luminance was 870 cd/$m^2$ at 5.5 V, the current efficiency was 55.22 cd/A, the power efficiency was 31.54 lm/W and the lifespan was 33 hours at 5,000 cd. Therefore, compounds according to embodiments of the present invention may be suitable for a material that is used to form an emissive layer of an organic light-emitting device.

A triazine-based compound according to an embodiment of the present invention, e.g., Compound 1, may exhibit a high energy gap because conjugation between two aryl groups in the biphenyl group substituted in the triazine ring is disturbed or removed. Accordingly, a triazine-based compound according to an embodiment of the present invention may be effectively used for a material that is used to form an organic layer suitable for fluorescent and phosphorescent devices for a variety of colors, e.g., red, green, blue and white, based on excellent electron transport and hole-blocking capabilities. Thus, embodiments of the present invention may provide an organic light-emitting device exhibiting high efficiency, low voltage, high luminance and long lifespan.

Exemplary embodiments of the present invention have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A triazine-based compound having three biphenyl groups, represented by structure 1, below,

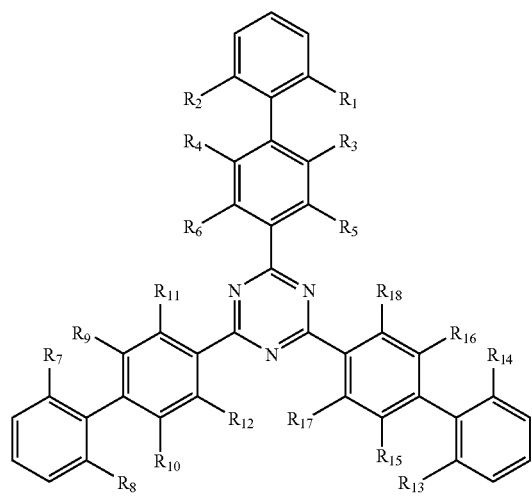

(1)

wherein $R_1$ through $R_{18}$ are each independently one of: hydrogen, a substituted $C_{1-30}$ alkyl group, an unsubstituted $C_{1-30}$ alkyl group, a substituted $C_{6-50}$ aryl group, an unsubstituted $C_{6-50}$ aryl group, a substituted $C_{4-50}$ heteroaryl group, and an unsubstituted $C_{4-50}$ heteroaryl group, and at least one of $R_1$, $R_2$, $R_7$, $R_8$, $R_{13}$ and $R_{14}$ is one of: a substituted $C_{1-30}$ alkyl group, an unsubstituted $C_{1-30}$ alkyl group, a substituted $C_{6-50}$ aryl group, an unsubstituted $C_{6-50}$ aryl group, a substituted $C_{4-50}$ heteroaryl group, and an unsubstituted $C_{4-50}$ heteroaryl group.

2. The compound as claimed in claim 1, wherein substituents of the alkyl group, the aryl group and the heteroaryl group include at least one of: —F; —Cl; —Br; —CN; —NO$_2$; —OH; a $C_{1-10}$ alkyl group that is unsubstituted; a $C_{1-10}$ alkyl group that is substituted with at least one of —F, —Cl, —Br, —CN, —NO$_2$ and —OH; a $C_{1-10}$ alkoxy group that is unsubstituted; a $C_{1-10}$ alkoxy group that is substituted with at least one of —F, —Cl, —Br, —CN, —NO$_2$ and —OH; a $C_{6-10}$ aryl group that is unsubstituted; a $C_{6-10}$ aryl group that is substituted with at least one of —F, —Cl, —Br, —CN, —NO$_2$ and —OH; a $C_{4-10}$ heteroaryl group that is unsubstituted; and a $C_{4-10}$ heteroaryl group that is substituted with at least one of —F, —Cl, —Br, —CN, —NO$_2$ and —OH.

3. The compound as claimed in claim 1, wherein $R_1$, $R_7$ and $R_{13}$ are identical, $R_2$, $R_8$ and $R_{14}$ are identical, $R_3$, $R_9$ and $R_{15}$ are identical, $R_4$, $R_{10}$ and $R_{16}$ are identical, $R_5$, $R_{11}$, and $R_{17}$ are identical, and $R_6$, $R_{12}$ and $R_{18}$ are identical.

4. The compound as claimed in claim 1, wherein one of $R_1$ and $R_2$ is a methyl group and the other is hydrogen, one of $R_7$ and $R_8$ is a methyl group and the other is hydrogen, and one of $R_{13}$ and $R_{14}$ is a methyl group and the other is hydrogen.

5. The compound as claimed in claim 4, wherein $R_3$, $R_4$, $R_5$, $R_6$, $R_9$, $R_{10}$, $R_{11}$, $R_{12}$, $R_{15}$, $R_{16}$, $R_{17}$, and $R_{18}$ are each hydrogen.

6. The compound as claimed in claim 1, wherein one of $R_1$ and $R_2$ is a phenyl group and the other is hydrogen, one of $R_7$ and $R_8$ is a phenyl group and the other is hydrogen, and one of $R_{13}$ and $R_{14}$ is a phenyl group and the other is hydrogen.

7. The compound as claimed in claim 6, wherein $R_3$, $R_4$, $R_5$, $R_6$, $R_9$, $R_{10}$, $R_{11}$, $R_{12}$, $R_{15}$, $R_{16}$, $R_{17}$, and $R_{18}$ are each hydrogen.

8. The compound as claimed in claim 1, wherein the substitutions of $R_1$ through $R_{18}$ are represented by one of structures 4 and 5, below,

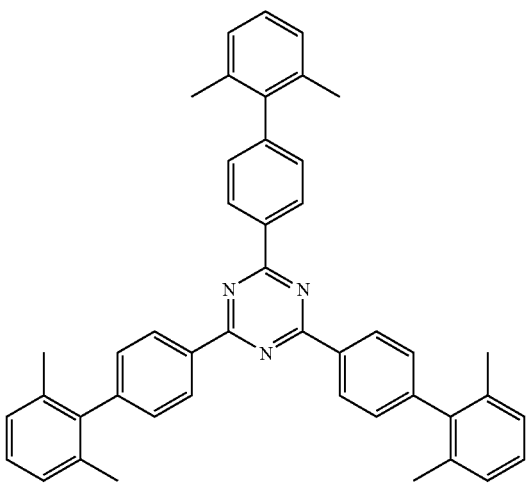

(4)

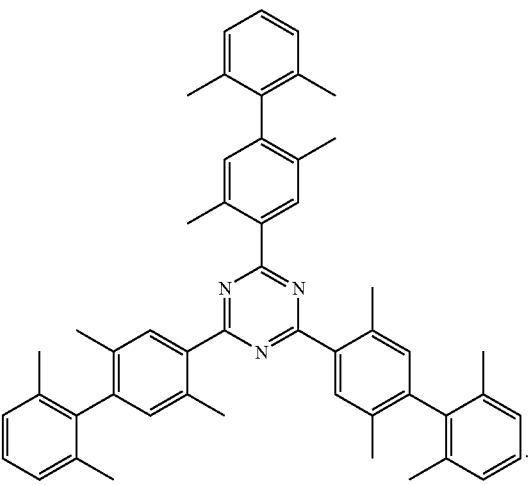

(5)

9. A method of making a triazine-based compound having three biphenyl groups, comprising:

reacting a triazine ring-containing compound with a first biphenyl compound such that the biphenyl compound is bonded to a carbon of the triazine ring, wherein:

the first biphenyl compound includes moieties $R_a$ and $R_b$:

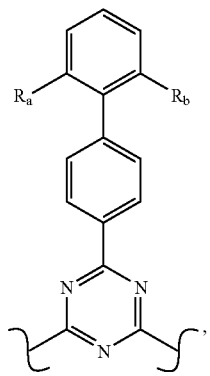

$R_a$ and $R_b$ are each independently one of: hydrogen, a substituted $C_{1-30}$ alkyl group, an unsubstituted $C_{1-30}$ alkyl group, a substituted $C_{6-50}$ aryl group, an unsubstituted $C_{6-50}$ aryl group, a substituted $C_{4-50}$ heteroaryl group, and an unsubstituted $C_{4-50}$ heteroaryl group, and at least one of $R_a$ and $R_b$ is: a substituted $C_{1-30}$ alkyl group, an unsubstituted $C_{1-30}$ alkyl group, a substituted $C_{6-50}$ aryl group, an unsubstituted $C_{6-50}$ aryl group, a substituted $C_{4-50}$ heteroaryl group, and an unsubstituted $C_{4-50}$ heteroaryl group.

10. The method as claimed in claim 9, wherein reacting the triazine ring-containing compound with the first biphenyl compound results in three identical biphenyl groups bonded to carbons of the triazine ring.

11. The method as claimed in claim 9, wherein the first biphenyl compound is prepared by reacting a first benzene ring-containing compound with a second benzene ring-containing compound, and the first benzene ring-containing compound includes:
   a reactive moiety attached to a first carbon of the benzene ring; and
   a second moiety attached to the benzene ring ortho to the reactive moiety, wherein the second moiety corresponds to one of $R_a$ and $R_b$ and is not hydrogen.

12. The method as claimed in claim 9, wherein the triazine ring-containing compound is a trihalotriazine.

13. An organic light-emitting device, comprising:
a first electrode;
a second electrode; and
at least one organic layer interposed between the first and second electrodes, wherein the at least one organic layer includes a triazine-based compound having three biphenyl groups, represented by structure 1, below,

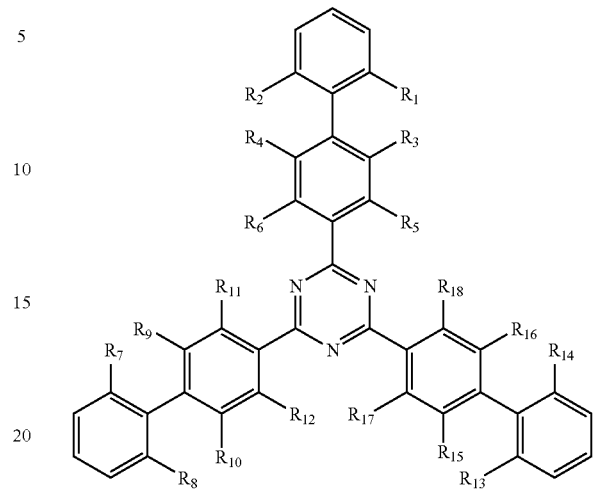

(1)

wherein $R_1$ through $R_{18}$ are each independently one of: hydrogen, a substituted $C_{1-30}$ alkyl group, an unsubstituted $C_{1-30}$ alkyl group, a substituted $C_{6-50}$ aryl group, an unsubstituted $C_{6-50}$ aryl group, a substituted $C_{4-50}$ heteroaryl group, and an unsubstituted $C_{4-50}$ heteroaryl group, and at least one of $R_1$, $R_2$, $R_7$, $R_8$, $R_{13}$ and $R_{14}$ is one of: a substituted $C_{1-30}$ alkyl group, an unsubstituted $C_{1-30}$ alkyl group, a substituted $C_{6-50}$ aryl group, an unsubstituted $C_{6-50}$ aryl group, a substituted $C_{4-50}$ heteroaryl group, and an unsubstituted $C_{4-50}$ heteroaryl group.

14. The organic light-emitting device as claimed in claim 13, wherein the at least one organic layer forms one of an emissive layer, a hole-blocking layer and an electron transport layer.

15. The organic light-emitting device as claimed in claim 14, wherein the at least one organic layer forms an emissive layer, and
the emissive layer includes a colored dopant.

16. The organic light-emitting device as claimed in claim 15, wherein the colored dopant is one of a red phosphorescent dopant, a green phosphorescent dopant, a blue phosphorescent dopant, a white phosphorescent dopant, a red fluorescent dopant, a green fluorescent dopant, a blue fluorescent dopant, and a white fluorescent dopant.

17. The organic light-emitting device as claimed in claim 14, wherein the at least one organic layer forms an emissive layer, and the device further comprises:
   a second organic layer that forms at least one of a hole-blocking layer and an electron transport layer, the second organic layer including the triazine-based compound having three biphenyl groups.

18. The organic light-emitting device as claimed in claim 17, wherein the organic light-emitting device structure is selected from the group consisting of: a first electrode/hole transport layer/emissive layer/electron transport layer/second electrode structure, a first electrode/hole injection layer/hole transport layer/emissive layer/electron transport layer/electron injection layer/second electrode structure, and a first electrode/hole injection layer/hole transport layer/emissive layer/hole-blocking layer/electron transport layer/electron injection layer/second electrode structure.

19. A triazine-based compound having three biphenyl groups, represented by structure 1 below:

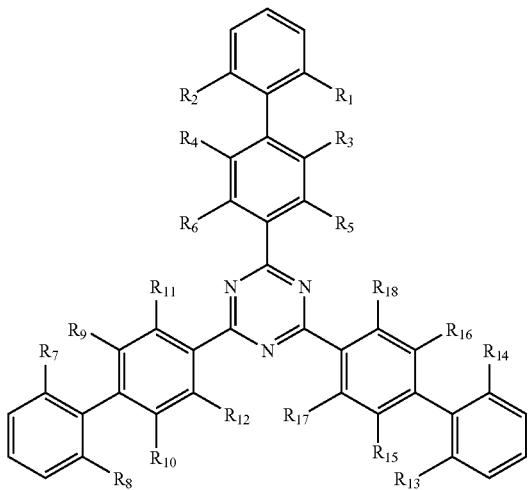

(1)

wherein $R_3$, $R_4$, $R_5$, $R_6$, $R_9$, $R_{10}$, $R_{11}$, $R_{12}$, $R_{15}$, $R_{16}$, $R_{17}$, and $R_{18}$ are, independently, one of hydrogen, an alkyl moiety of about 30 carbons or less, an aryl moiety of about 30 carbons or less, and a heteroaryl moiety of about 50 carbons or less, and at least one of $R_1$, $R_2$, $R_7$, $R_8$, $R_{13}$ and $R_{14}$ is a moiety effective to rotate the $C_1$-$C_1'$ bond of the biphenyl group to which it is attached, so as to disturb the conjugation between the rings of the biphenyl group.

20. The compound as claimed in claim 19, wherein the alkyl moiety of about 30 carbons or less is one of a substituted $C_{1-30}$ alkyl group and an unsubstituted $C_{1-30}$ alkyl group, the aryl moiety of about 30 carbons or less is one of a substituted $C_{6-50}$ aryl group and an unsubstituted $C_{6-50}$ aryl group, and the heteroaryl moiety of about 50 carbons or less is one of a substituted $C_{4-50}$ heteroaryl group and an unsubstituted $C_{4-50}$ heteroaryl group.

* * * * *